(12) United States Patent
Baldus et al.

(10) Patent No.: US 9,599,552 B2
(45) Date of Patent: Mar. 21, 2017

(54) DEVICES AND METHODS OF DETERMINING DISTURBANCE VARIABLE-CORRECTED ANALYTE CONCENTRATIONS

(71) Applicant: Roche Diabetes Care, Inc., Indianapolis, IN (US)

(72) Inventors: Susanne Baldus, Heppenheim (DE); Jochen Schulat, Mannheim (DE); Sebastian Trick, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 244 days.

(21) Appl. No.: 14/516,653

(22) Filed: Oct. 17, 2014

(65) Prior Publication Data

US 2015/0037898 A1 Feb. 5, 2015

Related U.S. Application Data

(63) Continuation of application No. PCT/EP2013/057999, filed on Apr. 17, 2013.

(30) Foreign Application Priority Data

Apr. 19, 2012 (EP) .................................. 12164805

(51) Int. Cl.
*G01N 21/27* (2006.01)
*G01N 33/50* (2006.01)
(Continued)

(52) U.S. Cl.
CPC ....... *G01N 21/272* (2013.01); *G01N 21/8483* (2013.01); *G01N 33/50* (2013.01);
(Continued)

(58) Field of Classification Search
CPC .. G01N 21/272; G01N 21/8483; G01N 33/48; G01N 33/50; G01N 33/66
(Continued)

(56) References Cited

U.S. PATENT DOCUMENTS 4,935,346 A 6/1990 Phillips et al.
5,049,487 A 9/1991 Phillips et al.
(Continued)

FOREIGN PATENT DOCUMENTS

CN 101006185 A 7/2007
EP 0302287 A2 2/1989
(Continued)

OTHER PUBLICATIONS

Banauch, D. et al., "A glucose dehydrogenase for glucose determination in body fluids," Z. Klim. Chem. Klin. Biochem., 1975, pp. 101-107.
(Continued)

*Primary Examiner* — Maureen Wallenhorst
(74) *Attorney, Agent, or Firm* — Stinson Leonard Street LLP

(57) ABSTRACT

Devices and methods are provided for determining concentration of at least one analyte in a body fluid sample such as blood, especially a blood glucose concentration. In the methods, a test element is provided that has at least one reagent element configured so as to carry out at least one optically detectable detection reaction in the presence of the analyte. The body fluid sample is applied to the test element and a time course of at least one optical measurement variable of the reagent element is detected. At least one first time interval of the time course of the optical measurement variable is used to determine at least one disturbance variable value in the body fluid sample, in particular a concentration of a disturbance variable such as hematocrit. At least
(Continued)

one second time interval of the time course is used to determine analyte concentration. The at least one disturbance variable value can be used to correct/compensate the analyte concentration.

18 Claims, 7 Drawing Sheets

(51) Int. Cl.
*G01N 33/66* (2006.01)
*G01N 21/84* (2006.01)

(52) U.S. Cl.
CPC .... *G01N 33/66* (2013.01); *Y10T 436/142222* (2015.01); *Y10T 436/144444* (2015.01)

(58) Field of Classification Search
CPC . Y10T 436/142222; Y10T 436/144444; Y10T 436/2575
USPC ............. 436/70, 93, 95, 164, 169, 171, 180; 435/14, 287.1, 287.7, 288.7; 422/400, 422/420, 68.1, 73, 82.05, 82.09, 502, 507
See application file for complete search history.

(56) References Cited

U.S. PATENT DOCUMENTS

| | | | |
|---|---|---|---|
| 5,246,858 A | | 9/1993 | Arbuckle et al. |
| 5,972,294 A | * | 10/1999 | Smith ...................... C12Q 1/54 422/422 |
| 7,553,615 B2 | | 6/2009 | Heindl et al. |
| 2005/0214891 A1 | | 9/2005 | Horn et al. |
| 2008/0003141 A1 | * | 1/2008 | Iketani ................. G01N 33/558 422/73 |
| 2010/0159570 A1 | | 6/2010 | Feldman et al. |
| 2010/0281219 A1 | | 11/2010 | Lippert et al. |
| 2011/0190607 A1 | | 8/2011 | Matzinger et al. |
| 2015/0268228 A1 | * | 9/2015 | Schulat .............. G01N 27/3274 435/29 |
| 2016/0011120 A1 | * | 1/2016 | Ringemann ........... G06F 19/707 436/95 |

FOREIGN PATENT DOCUMENTS

| | | |
|---|---|---|
| EP | 0354441 A2 | 2/1990 |
| EP | 0547710 A2 | 6/1993 |
| EP | 0821234 A2 | 1/1998 |
| EP | 1035919 B1 | 9/2000 |
| EP | 1035920 B1 | 9/2000 |
| EP | 1035921 B1 | 9/2000 |
| EP | 1039298 A2 | 9/2000 |
| EP | 1593434 A2 | 11/2005 |
| EP | 2259058 A1 | 12/2010 |
| EP | 2259258 A1 | 12/2010 |
| EP | 2325624 A1 | 5/2011 |
| JP | 1979082286 A | 6/1979 |
| JP | 19870206432 A | 8/1987 |
| JP | 19880101757 A | 4/1988 |
| JP | H03215746 A | 9/1991 |
| JP | H06506062 A | 7/1994 |
| JP | H10318928 A | 12/1998 |
| JP | 2004125775 A | 4/2004 |
| JP | 2006010706 A | 1/2006 |
| JP | 2007101482 A | 4/2007 |
| JP | 2007-303968 A | 11/2007 |
| JP | 2009233253 A | 10/2009 |
| JP | 2010522336 A | 7/2010 |
| WO | 2006023927 A1 | 3/2006 |
| WO | 2006/138226 A2 | 12/2006 |
| WO | 2007/012494 A1 | 2/2007 |
| WO | 2007/118647 A1 | 10/2007 |
| WO | 2008/114060 A1 | 9/2008 |
| WO | 2010/052307 A2 | 5/2010 |
| WO | 2010/094426 A1 | 8/2010 |
| WO | 2010/094427 A2 | 8/2010 |

OTHER PUBLICATIONS

Bergmeyer, Hans Ulrich, Editor, "Methods of Enzymatic Analysis," 1970, p. 417, 2nd edition, vol. 1, Verlag Chemie Weinheim.

Hoenes, Joachim et al., "The Technology Behind Glucose Meters: Test Strips," Diabetes Technology & Therapeutics, 2008, pp. S10-S26, vol. 10, Supplement 1.

Von Ketteler, Alexa et al., "Fluorescence Properties of Carba Nicotinamide Adenine Dinucleotide for Glucose Sensing," ChemPhysChem, 2012, pp. 1302-1306, vol. 13.

* cited by examiner

DEVICES AND METHODS OF DETERMINING DISTURBANCE VARIABLE-CORRECTED ANALYTE CONCENTRATIONS

CROSS-REFERENCE TO RELATED APPLICATIONS

This patent application is a continuation of Int'l Patent Application No. PCT/EP2013/057999 (filed 17 Apr. 2013), which claims priority to and the benefit of EP Patent Application No. 12164805.9 (filed 19 Apr. 2012). Each patent application is incorporated herein by reference as if set forth in its entirety.

TECHNICAL FIELD

This disclosure relates generally to engineering and medicine, and more particularly, it relates to devices and methods of determining concentration or presence of at least one analyte in a body fluid such as blood that use of a sudden wetting-induced change in a time course of an optical measurement variable detected on a test element for determining a disturbance variable in the blood.

BACKGROUND

A number of devices and methods for determining concentration or presence of one or more analytes in body fluids (e.g., blood, urine and saliva) are known in the art, including blood analyte measurement.

Specifically, test elements are known for rapidly and simply conducting such measurements that use at least one reagent element. Such reagent elements may be configured to carry out at least one detection reaction that is detectable in the presence of the at least one analyte such as, for example, a detection reaction that is optically detectable and/or a detection reaction that is electrochemically detectable. Possible reagent elements that may be used within the scope of this disclosure are disclosed in, for example, Hönes et al. (2008) *Diabetes Technol. Ther.* 10:10-26; as well as WO Patent Application Publication Nos. 2010/094426 and 2010/094427. A number of different kinds of test elements that include a reagent element also are known in the art. See, e.g., EP Patent Application Publication Nos. 0302287, 0547710 and 1593434.

In addition, EP Patent Application Publication No. 2325624 describes a device and method of assaying a body fluid. The object of the reference is to control a transmittance behavior of an optical transmittance system of a device by measuring at two different wavelengths. The method includes detecting diffuse reflectance curves at two different wavelengths. In the methods, measurement curves are subjected to fitting so that two fit curves are generated. An offset is determined from an intersection of the two fit curves (in the section between t1 and t2 in FIG. 5), and as described in, for example, paragraph [0030], an offset correction of the measurement values is conducted. The offset correction, as described in paragraph [0023], is necessary because the start time of sample application is uncertain and/or imprecise (e.g., paragraphs [0005]-[0006]), the transmittance behavior of the optical transmittance system may change upon applying the body fluid. A change in the reflectance behavior during wetting of the reagent element with the sample is not taken into account, as may be clearly seen in paragraph [0030], and the reflectance behavior during wetting is seen as constant.

U.S. Pat. No. 5,246,858 describes a device and a method of determining a reflectance of a reagent element that reacts with a body fluid component. In the method, the reagent element is irradiated with a radiation source, and the light reflected from the reagent element is determined. As may be seen in column 18, lines 18 ff., threshold value methods may be used to analyze the curve.

U.S. Pat. No. 5,049,487 describes a method of determining a presence of an analyte in a fluid. In the method, a reflectance measurement is conducted on a reagent matrix.

A practical problem frequently occurring in optical detection methods is as follows. While the actual detection reaction shows high specificity (i.e., only takes place in the presence of the analyte to be detected, not in the presence of other kinds of analytes), the detection of the reaction, which takes place based on a change in reflectance of the test field containing the reagent element, is influenced in many cases by one or more disturbance variables (e.g., specifically the percentage of red blood cells in a blood sample, i.e., the hematocrit value). As such, in blood glucose measurements using optical methods, the measurement values can depend on the hematocrit (Hct). This dependency also may be observed in electrochemical systems, which are generally correctable by a conductivity measurement and thus direct measurement of Hct.

Electrochemical devices and methods of analyte detection that take Hct into account are described in US Patent Application Publication No. 2010/0159570. The fill time of a test strip is used to determine the viscosity of the blood, and this in turn is used to determine Hct.

Similarly, JP Patent Application Publication No. 2007303968 describes a method of measuring an analyte in a blood sample that includes Hct correction. In this case, a test element with a filling channel is used, and a fill rate of the filling channel is determined. This fill rate in turn is used to determine Hct.

WO Patent Application Publication No. 2006/138226 describes a device for measuring blood glucose concentrations. In addition, a method is described in which Hct is determined from a time course of a change in a detector signal. Accordingly, a correction factor is selected depending on the Hct to calculate a glucose concentration.

WO Patent Application Publication No. 2008/114060 describes a device and method of determining a target substance in plasma of a whole blood sample without requiring removal of the red blood cells from the plasma prior to the test. In the method, an offset of an optical density is used to determine hemoglobin (Hb) concentration in the sample.

EP Patent Application Publication No. 2259058 describes a device and method of measuring Hct. In this case, a first measurement wavelength is used to determine Hb, and a second measurement wavelength is used to monitor an analyte-dependent color reaction.

U.S. Pat. No. 4,935,346 describes a method of determining presence of an analyte in a fluid sample. In this method, after a start time initiated by wetting, background measurement is conducted for correcting Hct at a preset first measurement time by means of a first light-emitting diode (LED) with a first wavelength of 700 nm. At a second measurement time, a second LED with a wavelength of 635 nm is used to measure glucose, and this measurement is corrected by Hct. In practice, however, this method is relatively expensive and requires a fairly high degree of expenditure on equipment. Optical measurements must be taken at different wavelengths at which the light is influenced differently by the actual detection reaction and Hct. Furthermore, the two optical measurements at different wavelengths are nevertheless influenced respectively by both Hct and blood glucose content. Even simple measurements of a background signal still show a relatively high degree of measurement uncertainty.

The continuing result of Hct dependency seen in conventional systems and methods, particularly photometric systems, is that despite the high operating expenses of known correction methods, the Hct range within which known systems and methods can be used is relatively narrow.

For the foregoing reasons, there is a need for additional devices and methods of determining an analyte concentration even when a disturbance variable is present in the sample.

BRIEF SUMMARY

An inventive concept described herein includes a recognition that an analyte concentration can be corrected for disturbance variable in a body sample via an optical detection reaction by detecting/measuring/monitoring a time course of at least one optical measurement value. This inventive concept is achieved by detecting at least two optical measurement variables obtained at two different time points during a first time interval and then using those two measurement variables to determine a disturbance variable concentration/value. In particular, a beginning of a sudden wetting-induced change (i.e., beginning time point) may be monitored and used as one time point during the first time interval, and the sudden wetting-induced change may be used to determine the disturbance variable based on a change in reflectance during the sudden wetting-induced change. A second, and typically subsequent, time interval of the time course of at least one optical measurement value is used to determine an analyte concentration or a corrected analyte concentration. This inventive concept can be incorporated into exemplary devices and methods as described herein and in more detail below.

It is therefore an object of the present disclosure to provide devices and methods that at least partially avoid the drawbacks of known devices and methods of determining at least one analyte concentration. This object can be attained by the devices and methods as described herein. In particular, devices and methods are provided for determining concentration or presence of at least one analyte in a body fluid sample that correct for disturbance variables with reduced equipment expenses but higher precision when compared to known devices and methods. Advantageous refinements of the inventive concept, which may be implemented individually or in any desired combinations, are presented in the claims.

For example, devices can include corresponding components and/or structures for determining an analyte concentration for at least one analyte even when a disturbance variable is present in a body fluid sample. Such devices include at least one optical detection device and at least one test element.

The optical detection device is configured so as to determine a time course of at least one optical measurement variable of the reagent element. In some instances, the at least one optical detection device can include at least one detector and at least one light source. In some instances, the light source is a single light source, such as an LED; in other instances, the light source is two or more light sources. The optical detector can be a photodiode.

The at least one test element can be in the form of a test strip. In some instances, the test strip has at least one capillary element for transferring the body fluid sample from an application site to a reagent element of the test strip, where the reagent element is configured for an optically detectable reaction.

The devices also can include at least one evaluation device, where the at least one evaluation device is configured to determine a disturbance variable value and analyte concentration from the time course of the optical measurement variable. In some instances, the at least one evaluation device is combined with the optical detection device as a test unit of the devices.

The devices can include a data processing unit having a volatile and/or non-volatile data storage unit.

Alternatively or additionally, the device may be configured by, for example, a presence of a corresponding partial device and/or devices, so as to carry out a method as described herein in one or more of the embodiments presented.

In view of the foregoing, the methods generally include determining a concentration (or even a presence) of at least one analyte in a body fluid sample. In some instances, the body fluid sample is blood, and the at least one analyte can be a metabolite. In certain instances, the at least one analyte is glucose, so that a blood glucose concentration can be detected.

The methods can begin by applying a body fluid sample to a test element. In some instances, the body fluid sample is blood, particularly a blood droplet. The body fluid sample can be applied to the test element at at least one sample receiving site. In some instances, the applying step occurs at a sample receiving site configured as an opening of a capillary element in the test element, especially when the test element is in the form of a test strip. The sample receiving site can be on a side of the test element opposite to a detection surface of a reagent element field, so that the test element has an application side and a detection side, with the detection surface being opposite to the application side. The body fluid sample can be automatically or manually applied to the test element.

The methods also include detecting/measuring/monitoring a time course of at least one optical measurement variable of the reagent element of the test element. In particular, this may be at least one optical measurement variable of a reagent element field according to the above description. The optical measurement variable may be influenced by the at least one optical property of the reagent element that can be influenced by the detection reaction. In particular, the optical measurement variable may be a reflectance value of the reagent element, such as a reagent element field including the reagent element, at one or more wavelengths, and a fluorescence signal of at least one fluorescence of the reagent element. The methods therefore use at least one optical measurement variable in the form of at least one reflectance value of a reagent element field including the reagent element.

In some instances, the time course of the at least one optical measurement variable may include a quantity of data in which respective measurement values are assigned to the relevant measurement times of the at least one optical measurement variable at which the optical measurement variables were determined/measured/monitored. In some instances, the time course of at least one optical measurement variable be subdivided into at least two time intervals of the time course of the optical measurement variable (i.e., two relevant measurement times).

The methods also include determining the concentration (or even a presence) of the at least one analyte in the body fluid sample, where the first time interval of the time course of the optical measurement variable can be used to determine at least one disturbance variable value in the body fluid sample, and the second time interval of the time course of the optical measurement variable can used to determine the analyte concentration in the body fluid sample.

In some instances, at least two optical measurement variables are obtained at two different time points during the first time interval and thus may be used when determining the disturbance variable value. In particular, a beginning of a sudden wetting-induced change (i.e., beginning time point) may be monitored and used as one time point during the first time interval, and the sudden wetting-induced change may be used to determine the disturbance variable value based on a change in reflectance during the sudden wetting-induced change. The wetting-induced change can be a characteristic variable such as, for example, a reflectance value during the wetting-induced change or during a portion of the sudden wetting-induced change.

The second time point during the first time interval can be an end of the sudden wetting-induced change (i.e., end time point). The end of the sudden wetting-induced change can be determined by comparing the at least one optical measurement variable or a change therein such as a temporal change with at least one threshold value.

To determine the at least one disturbance variable value from the characteristic variable, one may use a preset and/or determinable relation between the characteristic variable and the disturbance variable. In some instances, the disturbance variable can be cells, especially red blood cells (e.g., Hct).

As noted above, the second time interval of the time course of the optical measurement variable is used to determine the analyte concentration. Here, the time course of the same optical measurement variable used during the first time interval for determining the disturbance variable is observed.

In the methods, the time course of the optical measurement variable can be determined at a single wavelength of light. In some instances, the light source(s) therefore emit light at a wavelength in a range from about 300 nm to about nm 1100. In other instances, the wavelength can be about 365 nm, about 375 nm, about 440 nm, about 525 nm, about 550 nm, about 580 nm, about 635 nm, about 660 nm, about 740 nm, about 770 nm, about 815 nm or about 880 nm.

The methods may be carried out using a device as described herein in one or more of the described embodiments.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Corresponding reference characters indicate corresponding parts throughout the several views of the drawings.

Figure 1:
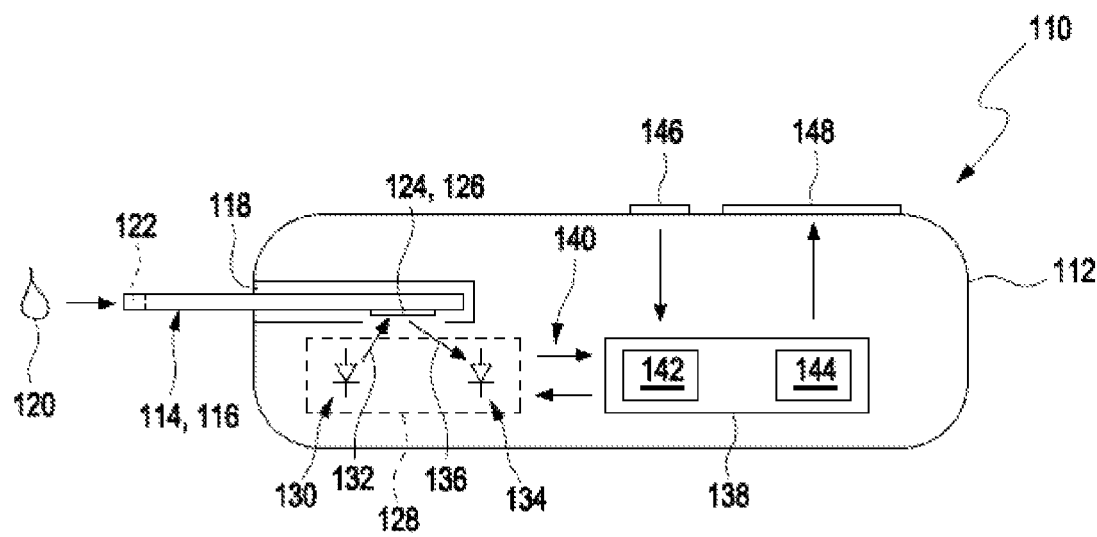
FIG. 1 shows a schematic sectional view of a device according to the invention with a test element and a test unit.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The devices and methods now will be described more fully hereinafter with reference to the accompanying drawings, in which some, but not all embodiments of the inventive concept are shown. Indeed, the devices and methods may be embodied in many different forms and should not be construed as limited to the embodiments set forth herein; rather, these embodiments are provided so that this disclosure will satisfy applicable legal requirements.

Likewise, many modifications and other embodiments of the devices and methods as described herein will come to mind to one of skill in the art to which the disclosure pertains having the benefit of the teachings presented in the foregoing descriptions and the associated drawings. Therefore, it is to be understood that the devices and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the devices and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

Devices and methods based upon the inventive concept are provided in which an analyte concentration can be corrected for a disturbance variable in a body fluid sample via an optical detection reaction by detecting/measuring/monitoring a time course of at least one optical measurement value. This inventive concept is achieved by detecting at least two optical measurement variables obtained at two different time points during a first time interval and then using those two measurement variables to determine a disturbance variable value. In particular, a beginning of a sudden wetting-induced change (i.e., beginning time point) may be monitored and used as one time point during the first time interval, and the sudden wetting-induced change may be used to determine the disturbance variable based on a change in reflectance during the sudden wetting-induced change. A second, and typically subsequent, time interval of the time course of at least one optical measurement value is used to determine an analyte concentration or a corrected analyte concentration.

As used herein, "sudden wetting-induced change" means a temporal change in the optical measurement variable that is caused by wetting of the reagent element or parts of the reagent element with blood or blood components.

As used herein, "disturbance variable," especially with respect to blood, means any influencing variable that constitutes a property of the blood, with the exception of the analyte concentration to be detected, wherein the property of the blood may influence determination of the analyte concentration. As explained above, the disturbance variable in particular may be an influencing variable that may vary according to the blood sample and influences detection and/or measurement of the at least one optical measurement variable. Alternatively or additionally, it may be an influencing variable that can influence the course of the detection reaction itself, for example in cases where the diffusion rates of one or more substances in the blood or blood components involved in the detection are influenced by the variable. In particular, the at least one disturbance variable may comprise a concentration of at least one disturbance component contained in the blood.

As used herein, "disturbance component" means a blood component, with the exception of the at least one analyte to be detected, which may influence determination of the analyte concentration. The disturbance component should be at least one component that is not involved in the detection reaction for detecting the analyte. Examples of disturbance components include, but are not limited to, cells such as red blood cells, white blood cells and even platelets.

In some instances, the disturbance variable is Hct of the blood. As used herein, "hematocrit" or "Hct" means a fraction of red blood cells in a whole blood sample. This fraction may be a volume fraction (e.g., a volume percentage of the red blood cells in whole blood). Alternatively or additionally, however, other disturbance components and/or disturbance variables may be determined.

The devices and methods are useful in a variety of applications. For example, such devices and methods can be used for determining blood glucose concentration or presence in a body fluid sample, such as a blood sample. In principle, however, the devices and methods also can be used to determine one or more other kinds of analytes, in particular determine one or more metabolites. Examples of analytes and metabolites include, but are not limited to, glucose, lactic acid, malic acid, glycerol, alcohol, cholesterol, triglycerides, ascorbic acid, cysteine, glutathione, peptides, urea, ammonium, salicylates, pyruvate, 5'-nucleotidase, creatine kinase (CK), lactate dehydrogenase (LDH), carbon dioxide, etc.

The devices and methods described herein have numerous advantages over known devices and methods. For one, efficient correction of disturbance variable effect(s), especially efficient Hct correction, can be carried out in optical blood glucose measurement. In contrast to known methods, which ordinarily involve high-level test requirements with respect to separation of red blood cells, the equipment expenses for converting to a method described herein can be kept extremely low for both the test element and the possible test unit. In particular, the methods may essentially be implemented in known units by means of corresponding software.

In contrast to EP Patent Application Publication No. 232562, in which reflectance behavior during wetting is seen as constant, as can be clearly seen for example in paragraph [0030], subdivision of the time course of the optical measurement variable of the sudden wetting-induced change can be used precisely for determining the disturbance variable value, especially a Hct value. The only purpose indicated in EP Patent Application Publication No. 2325624 is to change the transmittance behavior of an optical transmittance system by correcting application of the sample. Specifically, EP Patent Application Publication No. 2325624 does divide a time axis into several time intervals. In the time interval between the time points t1 and t2; however, no measurement values are determined, as can be clearly seen in, for example, Column 6, lines 2-6. In this time interval, only the successive measurement curves are extrapolated.

EP Patent Application Publication No. 2325624 therefore clearly fails to disclose the inventive concept herein that a time course of at least one optical measurement variable of the reagent element is determined in a first time interval, and at least one disturbance variable in the body fluid is determined from this time course in the first time interval. Specifically, in EP Patent Application Publication No. 2325624, no measurement curve is determined in the time interval between t1 and t2. Only the extrapolation curves are valid in this time interval.

Furthermore, these extrapolation curves are not used to determine a disturbance variable in the sample; rather, a start time and a change in the transmittance behavior of the optical transmittance systems are determined. As explained above, a disturbance variable is understood in particular to refer to any influencing variable that is a property of the body fluid sample, with the exception of the analyte concentration itself, and the property of the sample may influence determination of the analyte concentration. Therefore, the methods described herein make it possible, by subdivision of the actual measurement curve into at least two time intervals, to determine disturbance variables per se and/or reduce, compensate for, or correct their influence on determination of the analyte concentration.

Likewise, and in contrast to US Patent Application Publication No. 2010/0159570 A1 or JP Patent Application Publication No. 2007303968, the methods described herein determine a time course of an optical measurement variable of the reagent element itself. In this process, the optical measurement variable may be determined homogeneously and/or in a spatially averaged manner over the entire reagent element field and/or beyond the measurement area on the reagent element field, preferably without spatial resolution. For example, a single optical measurement variable at one site of a reagent element field including the reagent element or spatially averaged over one or more areas of the reagent element field may be detected in a time-resolved manner, and the time course of this optical measurement variable in the first time interval can be used to determine the disturbance variable value, and in the second time interval to determine the analyte concentration.

In other words, the methods described herein may be carried out without spatially resolved measurement of the at least one optical measurement variable and/or only with spatially averaged detection of the at least one optical measurement variable. In particular, the methods can be carried out without running time measurement and/or without fill time measurement of the test element, in particular without time-resolved measurement at different sites for determining a running time or fill time. Such simple optical measurements of at least one optical measurement variable of the reagent element, which in any case are usually provided by optical test elements, may be readily implemented without major equipment changes in the corresponding test units, in contrast to the fill time measurement described in US Patent Application Publication No. 2010/0159570 or JP Patent Application Publication No. 2007303968.

High-precision spatial resolution, which would be needed for fill time measurements and which would require complex equipment for implementation, may be dispensed with. Accordingly, one or more detectors of relatively simple design may be used with only one individual light source. In addition, fill time measurements always involve equipment problems as the time the sample is received is generally unknown, thus requiring that differential measurements be conducted on predetermined segments.

In detecting the time course of the at least one optical measurement variable, on the other hand, the influence of the disturbing variable is directly determined on the reagent element. In this case, as a rule, numerous physicochemical processes are simultaneously determined, such as diffusion processes, solvation, changes in index of refraction and other processes that are influenced by the disturbing variable. Detection is carried out directly at the location where the influence of the disturbing variable is to be determined, namely on the reagent element, in contrast to indirect measurements such as the aforementioned fill time measurements. As a rule, the physicochemical reactions and processes directly detected are those that can, based on the disturbance variable, and in particular the disturbance components, influence detection of the analyte in the reagent element.

The methods described herein make it possible, by means of the proposed subdivision of a time course of the optical measurement variable into at least one first time interval and at least one second time interval, to effectively separate determining the disturbance variable value and determining the analyte concentration. Surprisingly, it was found that by means of this temporal separation, favorable detection of the disturbance variable without any influence of the analyte concentration is possible even at one and the same wavelength.

In contrast, in U.S. Pat. No. 4,935,346, both the optical measurements at 700 nm and at 635 nm—although to different degrees—are affected by both the Hct value and the analyte concentration. Separation of these two effects can be achieved in practice only with difficulty. The temporal separation proposed herein overcomes this problem in a simple and elegant manner.

In particular, it is possible to measure the time course of the at least one optical measurement variable at only one wavelength in a simple manner and thus to determine both the disturbance variable value and the analyte concentration of an individual sample. Based on known or at least determinable influences of, for example, Hct value on analyte measurement, for example, glucose measurement, more efficient correction, such as mathematical correction, of the experimentally determined analyte concentration can be conducted either during evaluation or afterward in the form of a subsequent correction. The possibility of detecting the optical measurement value at only one wavelength provides a clear equipment-related advantage, as the use of several light sources can be avoided. Despite this, as stated above, several light sources may still be provided, for example, to recognize the start of a sudden wetting-induced change and thus determine a definite time point for the start time of the first time interval.

It was surprisingly found that a Hct value may be reliably determined based on a sudden wetting-induced change at a wavelength of about 880 nm. As determining glucose concentration is highly flexible with respect to the choice of the corresponding wavelength, the same wavelengths may be used for detecting the optical measurement variable during the first time interval and the second time interval. Therefore, only evaluating a single time course of a single optical measurement variable is required, which can considerably reduce the difficulty of evaluation and thus the demand on computing performance and resource requirements of an analysis device.

Moreover, the devices as described herein make it possible to sharply reduce expenses for equipment such as Hct-dependent photometric systems for analyte detection (e.g., photometric systems for blood glucose detection). This makes it possible to sharply increase, for example, the Hct ranges in which the device and method may be used without any significant increase in equipment expenses. This in turn allows significant expansion of the scope of application of devices through implementation of the methods as described herein. This expansion may be achieved in simple fashion by using novel evaluation software to implement the method.

The time course of the at least one optical measurement variable, for example the reflectance or relative reflectance (reflectance indicated as a ratio with respect to blank value reflectance) often is referred to as "kinetics", because this time course, at least in the second time interval, characterizes the course of the reaction for detection of the analyte. Evaluation and analysis of kinetic data shows a reliable correlation between disturbance variable value and this sudden wetting-induced change. This dependency was verified in various samples with a high degree of reproducibility. On this basis, determining Hct value of the sample used in particular is possible to take into account, either subsequently or even during evaluation, correction of the measurement value for the analyte concentration. In particular, it is possible in the methods to determine a disturbance variable value with an accuracy of plus or minus about 5% to about 10%, or alternatively better than about 5%. In the case of known dependency of the measured analyte concentration on Hct value, this makes it possible to carry out a mathematical correction or correction using a corresponding correction function and/or correction factors and/or correction offsets in a simple and reliable manner.

Devices

Devices incorporating the inventive concept can include corresponding components and/or structures for determining an analyte concentration for at least one analyte even when a disturbance variable is present in a body fluid sample. The devices may be configured to carry out a method as described herein or more of the variants presented in further detail below. As such, the devices include corresponding components and/or structures for executing all or several of the steps or to execute them out individually. In view thereof, such devices generally include at least one detection device and at least one test element.

The at least one detection device can be an electrochemical detection device or an optical detection device. In some instances, the at least one detection device is an optical detection device configured to determine a time course of at least one optical measurement variable of a reagent element of the at least one test element. As used herein, "optical detection device" means a device that, at several time points, can continuously or discontinuously determine the at least one optical measurement variable such as, for example, at least one optical measurement variable and store the variable(s) in a data storage unit.

For this purpose, the optical detection device can include one or more interrogating light sources for irradiating and/or illuminating the reagent element and/or impinging on the reagent element with at least one light beam. As used herein, "interrogating light beam" means a light beam by means of which a reagent element may be irradiated and which is suitable for eliciting any type of response from the reagent element. This response may be a reflection of the interrogating light beam, a scattering of the interrogating light beam, and/or a complete or partial absorption of the interrogating light beam, followed by re-emission and/or emission of another light beam. In some instances, the light source can be at least one first LED and at least one second LED, where the LEDs emit wavelengths in the ultraviolet, visible and/or infrared spectral regions. In other instances, the light source can be at least one laser diode. The light source therefore emits light at a wavelength in a range from about 300 nm to about nm 1100. In other instances, the wavelength can be about 365 nm, about 375 nm, about 440 nm, about 525 nm, about 550 nm, about 580 nm, about 635 nm, about 660 nm, about 740 nm, about 770 nm, about 815 nm or about 880 nm. If several light sources (e.g., LEDs) are provided, they may emit light simultaneously, in staggered fashion, or in a temporally overlapping manner.

As used herein, "about" means within a statistically meaningful range of a value or values such as a stated concentration, depth, length, molecular weight, pH, time frame, temperature, thickness, width or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

In view thereof, the optical detection device determines the at least one disturbance variable value and the analyte concentration at the same wavelength. Accordingly, the optical detection device may be configured so as to determine the optical measurement variable in a first time interval and a second time interval at the same at least one wavelength. As such, the same light source and/or the same detector (e.g., the same interrogating light source and the same detector) may be used to detect the optical measurement variable during the first time interval and the second time interval.

In addition to the one or more light sources, the at least one detecting device can include at least one optical detector for detecting at least one response light beam emitted by the reagent element, such as at least one semiconductor detector, for example, at least one photodiode. As used herein, "response light beam" means a light beam emitted from one of the reagent elements in response to the interrogating light beam. This emission may originate directly from the reagent element due to direct emission of photons of the response light beam by one or more molecules of the reagent element in the process of fluorescence and/or phosphorescence. Alternatively or additionally, the response light beam may originate from the reagent element in such a manner that it includes only a reflected or scattered interrogating light beam. In particular, the response light beam may include light from the interrogating light beam reflected or diffusely scattered by the reagent element. In some instances, the device may be configured so as to alternately detect reflected light of the LEDs with the same photodiode.

The at least one detection device also can include further elements such as, for example, at least one optical element, including at least one lens and/or at least one deflector element such as at least one mirror and/or at least one prism. Furthermore, the detection device may include one or more electronic components for activating and/or evaluating the at least one light source, at least one optional detector, the data storage and/or processing of signals of the at least one optional detector.

As noted above, the devices for determining an analyte concentration for at least one analyte even when a disturbance variable is present in a body fluid sample also include at least one test element for carrying out the detection reaction. As used herein, "test element" means any element by means of which qualitative and/or quantitative detection of the at least one analyte is possible, either when used alone or in conjunction with, for example, a test unit.

The test element includes the at least one reagent element, which can be configured for at least one optically detectable detection reaction. As used herein, "reagent element" means a material that includes one or more components and is configured to carry out at least one optically detectable detection reaction in the presence of an analyte of interest. The reagent element can include at least one enzyme that reacts specifically with the analyte of interest, especially at least one oxidase and/or at least one hydrogenase. Examples of enzymes include, but are not limited to, glucose oxidase and/or glucose dehydrogenase.

The reagent element may be configured so as to include the enzyme stabilized with a stable coenzyme, where the stabilized enzyme shows a reduction in enzymatic activity of less than about 50%, less than about 30%, or even less than about 20% when compared to the initial value in the course of storage of at least about two weeks, at least about four weeks, or even at least about eight weeks at a temperature of at least about 20° C., at least about 25° C., or even at least about 30° C., optionally at high humidity and without a drying reagent.

In addition to the enzyme, the reagent element can include at least one coenzyme. Examples of coenzymes include, but are not limited to, NAD, cNAD, PQQ and FAD. With respect to cNAD, reference may be made von Ketteler et al. (2012) *ChemPhysChem* 13:1302-1306, as well as the references cited therein.

In some instances, the reagent element therefore includes glucose dehydrogenase with NAD and/or with a stable NAD derivative such as, for example, cNAD, for detecting glucose, where a derivative of the reduced coenzyme NADH is formed. Alternatively or additionally, one or more of the coenzymes NAD, PQQ and FAD may be used. NADH can be detected by optical methods (e.g., by photometric or fluorometric determination after UV excitation). An exemplary test system is described in US Patent Application Publication No. 2005/0214891.

Furthermore, the reagent element can include at least one mediator and/or at least one dye/optical indicator that may indicate the course of the enzymatic detection reaction by means of a reflectance measurement and/or a fluorescence measurement. Examples of mediators for optically detecting analytes include, but are not limited to, nitrosoaniline, (e.g., [(4-nitrosophenyl)imino]dimethanol-hydrochloride), quinones (e.g., phenanthrene quinones, phenanthroline quinones or benzo[h]-quinoline quinones), phenazines (e.g., 1-(3-carboxypropoxy)-5-ethyl phenazinium trifluoromethane sulfonate) and/or diaphorase (EC 1.6.99.2). Examples of phenanthroline quinones include 1,10-phenanthroline-5,6-quinones, 1,7-phenanthroline-5,6-quinones, 4,7-phenanthroline-5,6-quinones and their N-alkylated or N,N'-dialkylated salts, where in the case of N-alkylated and/or N,N'-dialkylated salts halides, trifluoromethane sulfonate or other solubility-increasing anions can be used as counterions. Examples of optical indicators include, but are not limited to, heteropolyacids such as 2,18-phosphomolybic acid.

The reagent element therefore includes at least one reagent that converts the analyte in a detection reaction, especially at least one enzymatic detection reagent. Examples of such analyte-specific enzymatic detection reagents include, but are not limited to, oxioreductase enzymes (e.g., GlucDor/PQQ), dehydrogenase enzymes, oxidase enzymes or similar enzymes or combinations of the aforementioned and/or other enzymes such as glucose oxidase (GOD) or glucose dehydrogenase (GDH) (including FAD-, NAD+- or PQQ-dependent). In some instances, the enzymes may be a mutant enzyme. For example, WO Patent Application Publication No. 2007/118647 describes a reagent element based on using a coenzyme PQQ-dependent GDH-mutant (EC 1.1.5.2). Further examples of a PQQ-dependent reagent element that may be used in the reagent element are described in EP Patent No. 0354441.

Regardless of its components, the reagent element facilitates at least one detectable reaction that may be an electrochemically and/or optically detectable reaction, especially an optically detectable reaction. In particular, this may be a reaction in which at least one substance to be detected is formed in the presence of the at least one analyte. In this manner, several substances to be detected may be formed and/or used, and they may be detected individually, in groups or altogether. As such, substances to be detected are substances that form as the result of the at least one detection reaction and/or are involved in the at least one detection reaction and are directly or indirectly detectable. After detection, the at least one substance to be detected may be used to quantitatively and/or qualitatively determine the at least one analyte. Examples of the reagent element and/or substance to be detected may be found in WO Patent Application Publication No. 2010/052307.

When the reagent element is in the form of a reagent element layer, it may contain further substances such as, for example, one or more fillers, including one or more kinds of particles, such as inorganic particles. The particles are not identical to the components of the reagent element or at least not completely identical thereto. The reagent element also may include a mixture of several detection reagents or several substances, which together may form the reagent element layer. The reagent element layer therefore may be configured analogously to the first film layer of the diagnostic test carrier described in EP Patent No. 0821234. Thus, the detection layer and/or the reagent element layer may include, for example, at least one organic film-forming agent. The at least one film-forming agent may include a polyvinyl propionate dispersion. Alternatively or additionally, other film-forming agents may be used.

The reagent element therefore can be located in at least one reagent element layer or detection layer of the test element. Reagent element layer and detection layer are used synonymously. Moreover, the reagent element can be a component of a reagent element field, and/or the test element may include at least one reagent element field, which may include the at least one reagent element. As used herein, "reagent element field" means a cohesive unit such as, for example, a cohesive layer incorporating the reagent element or completely consisting of the reagent element. This layer may have a thickness, especially a dry layer thickness, from about 0.5 µm to about 500 µm, or from about 10 µm to about 100 µm.

The reagent element field may have at least one detection surface and/or at least one test field window that is optically accessible from the outside (e.g. that can be observed by means of at least one optical detection step) so that the at least one optically detectable detection reaction can be detected via this surface.

The reagent element also should be capable of being sufficiently stable to withstand, at least in the short term, humidity and thermal loading (e.g., temperatures of at least about 60° C., at least about 70° C. at least about 80° C., at least about 90° C., at least about 100° C., at least about 110° C., or even at least about 120° C.).

With respect to possible reagent elements, reference may be made to the following: WO Patent Application Publication Nos. 2007/118647, 2010/094426 and 2010/094427; EP Patent No. 0354441; Hönes et al. (2008), supra and von Ketteler et al. (2012), supra.

As noted above, in some instances, the reagent element is a thermostable reagent element. A reagent element that is configured to be at least temporarily stable at the above-mentioned temperatures has a thermal stress duration of at least about 1 minute to at least about 5 minutes, shows a decrease in its activity at the elevated temperatures of less than about 50%, less than about 40%, less than about 30%, or even less than about 20%. For example, the reagent element may be exposed for the aforementioned durations to the elevated temperatures in the form of a dry reagent element on the carrier element to test these properties. Activity is determined before or after the thermal stress. In principle, the activity may be determined by means of any method known in the art, as within the scope of the present definition, only the percent decrease in activity during thermal stress is relevant. The activity may relate specifically to enzyme activity of the reagent element, especially a dry reagent element in a test strip. For example, methods are known in which the enzyme activity is measured by extracting the enzyme from the reagent element and/or the test element, and then determining the activity by means of ultraviolet absorption. See, e.g., Bergmeyer: Methoden der enzymatischen Analyse (Methods of Enzymatic Analysis), Verlag Chemie 417 ($2^{nd}$ ed. 1970) or Banauch et al. (1975) Z. Klin. Chem. Klin. Biochem. 13:101-107. For example, to test for stability and/or decrease in activity, a test element such as a test strip may be manufactured with the reagent element. The enzyme activity of an enzyme of the reagent element is then measured by a commonly-used method, followed by the storage at elevated temperature, and then measurement of enzyme activity by the same method. The process is ordinarily carried out using a representative group of test elements and/or reagent elements.

Examples of thermostable reagent elements can be found in the following: WO Patent Application Publication Nos. 2007/012494, 2010/094426 and 2010/094427; and von Ketteler et al. (2012), supra. The reagent elements presented in these references may be used alone or in combination with one or more other reagent elements. Alternatively or additionally, however, other reagent elements also can be used.

As mentioned above, the reagent element may contain at least one enzyme and at least one coenzyme, especially at least one stable coenzyme, which are stored together. By using a stable coenzyme, it is possible to conduct temperature stabilization and/or long-term stabilization of several weeks and/or months at high relative humidity or even in liquid phase and at elevated temperatures. This finding is surprising, as it is known that although enzymes in the presence of a native coenzyme possess increased short-term stability for a few hours, they show poor shelf life over longer periods. In view of these findings, which are not consistent with prior art, it was surprising that an enzyme in the presence of a stable coenzyme showed sharply higher thermal and long-term stability than an enzyme in the presence of a native coenzyme, particularly as the stable coenzymes have a lower binding constant with the enzyme than the native coenzyme.

The enzyme, especially the enzyme stabilized by the coenzyme, may be a coenzyme-dependent enzyme. Examples of suitable enzymes include dehydrogenases such as glucose dehydrogenase (E.C.1.1.1.47 and/or E.C.1.1.5.2), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1), alpha-hydroxybutyrate dehydrogenase, sorbitol dehydrogenase, or amino acid dehydrogenases such as L-amino acid dehydrogenase (E.C.1.4.1.5). Further suitable enzymes are oxidases such as glucose oxidase (E.C.1.1.3.4) or cholesterol oxidase (E.C.1.1.3.6) and/or aminotransferases such as aspartate or alanine aminotransferase, 5'-nucleotidase or creatine kinase. In some instances, glucose is detected by means of glucose dehydrogenase (GDH).

The use of a mutant GDH has been found to be particularly advantageous. In this respect, reference may be made to WO Patent Application Publication No. 2007/118647. As used herein, "mutant" means a genetically modified variant of a native enzyme that has the same number of amino acids but an amino acid sequence that has been modified compared to the wild-type enzyme (i.e., that differs in at least one amino acid when compared to the wild-type enzyme). The mutation(s) may take place site-specifically or non-site-specifically, and if site-specifically by using recombination methods known in the art, where in accordance with the respective requirements and conditions, at least one amino acid exchange within the amino acid sequence of the wild-type enzyme occurs. In some instances, the mutant shows increase thermal or hydrolytic stability when compared to the wild-type enzyme.

Mutant glucose dehydrogenases contain modified amino acid(s) when compared to the corresponding wild-type GDH at any desired position of the wild-type amino acid sequence. In some instances, the mutant GDH has a mutation at at least one of positions 96, 170 and 252 of the amino acid sequence of wild-type GDH, where mutants with mutations at position 96 and position 170 and/or mutations at position 170 and position 252 are advantageous. In some instances, the mutant GDH has no further mutations other than these.

The mutations at the positions 96, 170 and 252 may include any desired amino acid exchange that leads to stabilization (e.g., an increase in thermal or hydrolytic stability) of the wild-type GDH. In some instances, the mutation includes an amino acid exchange at position 96 of glutamic acid for glycine, while with respect to position 170 an amino acid exchange of glutamic acid for arginine or lysine or alternatively glutamic acid for lysine. In other instances, the mutation includes an amino acid exchange at position 252 of lysine for leucine.

The mutant GDH may be obtained via mutation of wild-type GDH from any desired biological source. As used herein, "biological source" means both prokaryotes (i.e., bacteria) and eukaryotes (e.g., mammals and other animals). In some instances, the wild-type GDH is from a bacterium such as, for example, *Bacillus megaterium*, *Bacillus subtilis* or *Bacillus thuringiensis*, especially *B. subtilis*. In some instances, the mutant GDH obtained by mutating wild-type GDH from *B. subtilis* (e.g., GlucDH_E96G_E170K or GlucDH_E170K_K252L).

The stable coenzyme can be a chemically modified coenzyme when compared to the native coenzyme that shows higher stability (e.g., hydrolytic stability) than the native coenzyme. The stable coenzyme is stable under test conditions with respect to hydrolysis. When compared to the native coenzyme, the stable coenzyme shows a decreased binding constant for the enzyme, for example, a binding constant decreased by a factor of 2 or more. Examples of stable coenzymes include, but are not limited to, stable derivatives of nicotinamide adenine dinucleotide (NAD/NADH) or nicotinamide adenine dinucleotide phosphate (NADP/NADPH) or truncated NAD derivatives (e.g., without the AMP moiety or with non-nucleoside residues such as hydrophobic residues). Alternatively, the stable coenzyme can be a compound of Formula (I).

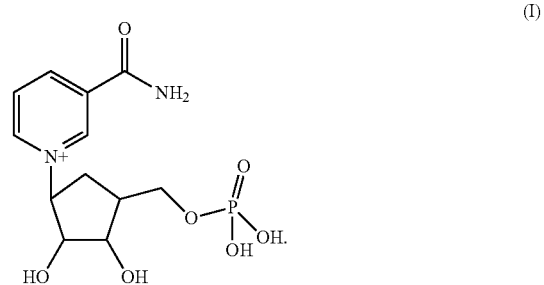 [SMILES: NC(=O)c1ccc[n+](C2CC(COP(=O)(O)O)C(O)C2O)c1]

Other stable derivatives of NAD/NADH and NADP/NADPH are described in the above-mentioned references, as well as in WO Patent Application Publication No. 2007/012494 and US Patent Application Publication No. 2007/0026476, In other instances, the stable coenzyme can be a compound of general Formula (II):

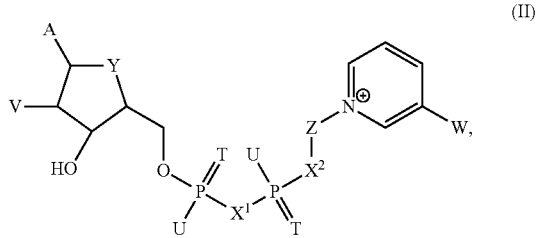

where:
A=adenine or an analog thereof,
T=independently O, S respectively,
U=independently OH, SH, $BH_3^-$, $BCNH_2^-$ respectively,
V=independently OH or a phosphate group respectively, or two groups that form a cyclic phosphate group;
W=COOR, $CON(R)_2$, COR, $CSN(R)_2$ with R=independently H or $C_1$-$C_2$-alkyl respectively,
$X^1$, $X^2$=independently O, $CH_2$, $CHCH_3$, $C(CH_3)_2$, NH, $NCH_3$ respectively,
Y=NH, S, O, $CH_2$, and
Z=a linear or cyclic organic residue, with the proviso that Z and the pyridine residue are not linked by a glycoside bond, or a salt or if applicable, a reduced form thereof.

In the compounds of Formula (II), Z can be a linear residue with 4-6 C atoms, especially 4 C atoms, where 1 or 2 C atoms are optionally substituted by one or more heteroatoms selected from O, S and N, or a residue including a cyclic group with 5 or 6 C atoms, which optionally contains a heteroatom selected from O, S and N and optionally contains one or more substituents, and a residue $CR^4_2$, where $CR^4_2$ is bonded to the cyclic group and $X^2$, with $R^4$=independently H, F, Cl, $CH_3$ respectively.

In some instances, Z is a saturated or unsaturated carbocyclic or heterocyclic five-membered ring, in particular a compound of general Formula (III):

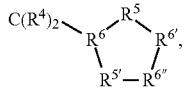

where:
a single or double bond may be present between $R^{5'}$ and $R^{5''}$,
$R^4$=independently H, F, Cl, $CH_3$ respectively,
$R^5$=$CR^4_2$,
$R^{5'}$=O, S, NH, $NC_1$-$C_2$-alkyl, $CR^4_2$, CHOH, $CHOCH_3$,
$R^{5''}$=$CR^4_2$, CHOH, $CHOCH_3$ if a single bond is present between $R^{5'}$ and $R^{5''}$,
where $R^{5'}$=$R^{5''}$=$CR^4$ if a double bond is present between $R^{5'}$ and $R^{5''}$, and
$R^6$, $R^{6'}$=independently CH or $CCH_3$ respectively.

In some instances, the compounds according to the invention comprise adenine or adenine analogs such as $C_8$- and $N_6$-substituted adenine, deaza variants such as 7-deaza, aza variants such as 8-aza or combinations such as 7-deaza or 8-aza or carbocyclic analogs such as formycin, where the 7-deaza variants may be substituted at the 7-position with halogen, $C_1$-$C_6$-alkinyl, -alkenyl or -alkyl.

In other instances, the compounds include adenosine analogs that have instead of ribose, a 2-methoxydeoxyribose, 2'-fluorodeoxyribose, hexitol, altritol and/or polycyclic analogs such as bicyclo-, LNA- and tricyclo-sugars.

Moreover, in compounds of Formula (II), the (di-)-phosphate oxygens may be substituted (e.g., isotronically and/or isovalently and/or isoelectronically substituted, i.e., O— by S— and/or $BH_3^-$, O by NH, $NCH_3$ and/or $CH_2$ and =O by =S). Furthermore, in compounds of Formula (II), W can be $CONH_2$ or $COCH_3$.

In compounds of Formula (III), $R^5$ can be $CH_2$. Moreover, $R^{5'}$ can be $CH_2$, CHOH and NH. Furthermore, $R^{5'}$ and $R^{5''}$, respectively, can be CHOH. Alternatively, $R^{5'}$ is NH and $R^{5''}$ is $CH_2$.

In certain instances, the coenzyme is cNAD or "carbaNAD" according to one or more of Formulas (I), (II) or (III) above. Alternatively or additionally, the coenzyme may include one or more coenzymes selected from NAD, cNAD, PQQ and FAD.

In view thereof, the reagent element is configured so that the enzymes contained therein are stabilized for long periods. This means that the enzyme stabilized with a stable coenzyme as, for example, a dry matter, is stored for a duration of at least about two weeks, at least about four weeks, or even at least about eight weeks, where the enzyme activity decreases by less than about 50%, by less than about 30%, or even by less than about 20% with respect to the initial values for enzyme activity.

By stabilizing the enzyme, it is possible to store the enzyme stabilized with a stable coenzyme for long periods, even without a drying reagent, as indicated above, and/or at high temperatures, as indicated above. Moreover, the stabilized enzyme may be stored at high relative humidity (e.g. relative humidity of at least about 50%), where the enzyme activity decreases by less than about 50%, by less than about 30%, or even by less than about 20% with respect to the initial values.

In addition, the enzyme stabilized with a stable coenzyme may on the one hand be stored as dry matter and on the other hand in liquid phase. In some instances, the stabilized enzyme is stored on or in the test element that is suitable for determining an analyte. The enzyme stabilized with a stable coenzyme therefore forms a component of the reagent element, which may optionally also include further components such as salts, buffers, etc. In other instances, the reagent element is free of a mediator.

The enzyme stabilized with a stable coenzyme may generally be used for detecting analytes, for example parameters in body fluids such as blood, serum, plasma or urine and/or in waste water samples or food products.

The test element may contain at least one carrier element to which the at least one reagent element is connected. In some instances, this may be a carrier element in the form of a strip, a band and/or a disk. The carrier element may be manufactured wholly or partially from a paper material, a plastic material and/or a ceramic material and can include one or more layers. In other instances, the test element can be in the form of a cassette, magazine, swab or sheet, where one or more reagent element fields are provided for each test unit, and where the magazine may be configured as a test strip magazine (such as a stacking magazine), as a tape cassette or a plate magazine. Such cassettes, magazines and test elements, as well as test units, are generally known to one of skill in the art.

The reagent element thus can be bonded to the carrier element by directly or indirectly applying the reagent element in the form of at least one reagent element layer to the carrier element. Examples of bonding include, but are not limited to, blade coating, printing (in particular screen printing, stencil printing or pad printing) and spin coating.

In some instances, the carrier element may be manufactured wholly or partially from at least one plastic material. Specifically, this plastic material may be a plastic material with a softening temperature determinable according to DIN EN ISO 306 of at least about 100° C., at least about 110° C., at least about 120° C., at least about 130° C., at least about 140° C., or even at least about 150° C. Examples of such plastics include, but are not limited to, acrylonitrile-butadiene-styrene (ABS), polymethyl methacrylate (PMMA), polypropylene (PP), polyester and polycarbonate (PC) or combinations of the aforementioned and/or other plastics. In principle, however, other plastics may also be used.

In addition, the carrier element may include at least one film element, which may be a plastic film. This film may have a single-layer or multilayer structure. Moreover, the carrier element may support one or more reagent elements. For example, the reagent element may provide at least one accessible test field surface for receiving a sample.

In some instances, the test element having the at least one reagent element may be a single-use test element and/or at least one single-use test element (i.e., a test element configured for exactly one detection of the analyte and then discarded). The test element may be configured in strip form as a test strip; however, other embodiments also are possible.

In view thereof, the test element may be individually prepared by a user by inserting the test element into the test unit of the device. Alternatively or additionally to individual manual insertion of the test element into the test unit, the test unit may be configured to store and/or to provide a plurality of test elements from at least one cassette or magazine. For example, the test unit may be configured to bring individual test elements from the at least one cassette or magazine into an application position by means of a suitable actuator.

When the test element is in the form a test strip, the device may include at least one test strip holder, such as a mechanical device configured to hold the test strip. In this manner, at least one test strip in the test strip holder may be moved into an application position, where in the application position at least one application site of the test strip is accessible to a user for application of the body fluid sample. The at least one test strip may be placed in the test strip holder and moved into the application position externally (e.g., from outside of the test unit, manually by a user) by sliding a test strip into the test strip slot of the holder. Alternatively or additionally, a test strip may be placed in the test strip holder and moved into the application position from a space inside the test unit of the device and/or from a cassette or magazine.

In the application position, the test element may be configured in such a way that at least one sample receiving site and/or application site of the test element, at which the body fluid sample (e.g., a blood droplet) can be placed on the test element, is accessible to a user. Moreover, and as mentioned above, the test element may include at least one sample receiving site or application site at which the body fluid sample can be placed on the test element. For example, this may be a field to which the sample is applied.

In certain instances, the methods described herein may be carried out in such a way that the body fluid sample is applied to at least one sample receiving site on the test element. This sample receiving site may be directly configured on the reagent element or configured at a distance from the reagent element by at least about 1 mm, at least about 2 mm, or alternatively from about 3 mm to about 10 mm. In particular, when the sample receiving site is configured at a distance from the reagent element, the body fluid sample may be transferred from the sample receiving site to the reagent element. At least one transfer element, which may be a component of the test element or a component of a test unit operating jointly with the test element, can be provided for this purpose. In some instances, the transfer element has at least one capillary element, which may be a component of the test element and may be configured so as to transfer, by means of capillary forces, the body fluid sample or components thereof from the at least one sample receiving site to the reagent element (e.g., a reagent element field including the reagent element).

Alternatively or additionally, the sample receiving site may include an opening of at least one capillary element. The capillary element may be provided between the sample receiving site and the reagent element. In some instances, this capillary element may include a capillary gap having a length of at least about 0.5 mm or even at least about 5 mm. Alternatively, the length can be from about 5 mm to about 50 mm, or even from about 10 mm to about 20 mm. In addition, the capillary element may have a cross section of less than about 1 mm or alternatively a cross section of about 50 µm to about 1000 µm. The capillary element can have a capillary channel with a square, polygonal or round cross section with a diameter or equivalent diameter of less than about 1 mm or even less than about 200 µm. In some instances, capillaries having a square cross section can be used with side measurements of about 1.5 mm×75 µm or even smaller dimensions such as about 0.5 mm×50 µm.

The test element also can include at least one separating element for separating at least one cellular component such as blood cells from the body fluid sample and may be configured between the capillary element and the reagent element. In this manner, the separating element may include at least one separating layer. For example, the capillary channel may be configured to open onto an edge and/or a surface of the separating layer and transfer blood or blood components to the site in question. From this site, blood or blood components may then penetrate the separating layer. After penetrating the separating layer, the blood or blood components, optionally after separation of one or more components, can be directly or indirectly transported to a reagent element layer that includes the reagent element. Specifically, a layered structure may be used in which, moving outward from the capillary, at least one separating layer is first used, followed by at least one reagent element layer. The separating element and/or the separating layer typically does not include reagent elements, and should not be involved in the detection reaction. Other arrangements for a separating element and/or the separating layer are known in the art.

The at least one separating element may include at least one separating layer and/or at least one sieve and/or at least one fabric and/or at least one non-woven. The at least one separating element may be a component of a layered structure that may include the reagent element. The at least one separating element may be configured as a separating layer, where the body fluid or components thereof on the path from the sample receiving site to the reagent element layer must first pass through at least one separating element layer. Such separating elements are generally known in the art. In particular, the separating element may include at least one separating layer that is in contact with the reagent element.

The test element may be configured in such a way that an interrogating light beam in the reagent element can impinge upon it. For this purpose, the reagent element field may have a surface assigned to the detection device. Specifically, the test strip may be configured so that an incident interrogating light beam entering the reagent element may first pass through the reagent element (e.g., through at least one reagent element layer) then pass through the separating element (e.g., through at least one separating layer), then be reflected by at least one reflecting surface, pass again through the separating element, once again pass through the reagent element, and finally exit the test element in the form of a response light beam. The reflection by the reflecting surface may be reflection from a reflecting surface of a carrier element of the test element. To increase the reflectivity of the surface, the carrier element may contain one or more pigments such as titanium dioxide.

By means of the above-described reflective structure, the light passes through the reagent element on its path through the test element at least twice, as single or even multiple reflections are possible. Accordingly, the light is influenced at least twice by the reagent element, which can increase the sensitivity of optical detection. However, the light also passes through the separating element multiple times, so that separated blood components, which may accumulate on or in the separating element, can also influence the light multiple times. The light also may be influenced to an increased degree by a disturbance component accumulated in or on the separating element, such as red blood cells. This in turn means that the sensitivity of optical detection of the disturbance component during the first time interval may also be increased.

The reflecting surface may be directly configured on the separating element. Alternatively, the reflecting surface may be configured at a distance from the separating element. For example, a section of the capillary element may be positioned between the separating element such as a separating layer and the reflecting surface so that the light may pass through a part of a capillary channel of the capillary element between the separating element and the reflecting surface.

The test element, especially a test strip, can have at least one field of the reagent element that is visible from outside the test element. In this manner, the optical detection device may be configured to detect the at least one optical property of the reagent element in the reagent element field. The reagent element field can provide the aforementioned surface via which the reagent element can be irradiated with interrogating light and via which response light can be emitted from the reagent element.

In addition to the detection device and the test elements, the overall devices also can include at least one evaluation device configured to determine at least one disturbance variable in the body fluid sample (e.g., Hct in a blood sample) from at least one first time interval of a time course of the optical measurement variable. The evaluation device also can be configured to detect the concentration of the at least one analyte from at least one second time interval of the time course of the optical measurement variable.

If several LEDs are provided, the evaluation device may be configured so as to use the light reflected by the second LED to recognize wetting of the reagent element by the body fluid or components thereof. This recognition of the wetting may take place via monitoring of a reflectance value. Specifically, a reflectance value of light emitted by the second LED may be compared on a reagent element field with one or more threshold values, wherein a major change in reflectance indicates the start of wetting and of a sudden wetting-induced change. The evaluation device also may be configured so as to use reflected light from the first LED to detect an optical measurement variable, especially a reflectance value, during the first time interval and second time interval, and from this to determine the at least one disturbance variable value in the body fluid sample, such as the at least one analyte concentration.

For this purpose, the evaluation device may include one or more electronic components such as, for example, at least one data processing unit, especially a microcomputer. The data processing unit may be programmatically configured to carry out one or more of the steps of the methods described herein. Thus, the data processing unit may be configured using a programming code to implement a method to determine at least one disturbance variable in the blood from the first time interval of the time course of the optical measurement variable and to determine the concentration of the at least one analyte from the second time interval of the time course of the optical measurement variable.

The data processing unit further can include at least one volatile and/or non-volatile data storage unit. Analyte concentrations may be stored and/or a database may be deposited in the data storage unit. Likewise, comparison patterns and/or comparison curves for evaluating the time course of the optical measurement variable in the first time interval and/or the second time interval may be deposited in the data storage unit. The patterns and/or curves can be used to carry out one or more of the pattern comparison steps or evaluation steps in the methods as described herein. Moreover, one or more corrections, such as correction tables, may be stored in the data storage unit to optionally carry out correction of the analyte concentration in accordance with the ascertained disturbance variable in the body fluid sample.

In some instances, the at least one detection device and/or the at least one evaluation device can be incorporated into a test unit.

The test unit can include other operating elements. Specifically, the device may include a test unit that may operate together with the at least one test element. To operate in conjunction with the test element, the test unit can have a test element holder and/or a test element applicator configured to bring the test element into an application position in which the body fluid sample can be applied. Alternatively or additionally, application of the body fluid sample may be conducted with the test element separated from the test unit. Mixed configurations are also conceivable such as, for example, a device in which the test element is first connected to the test unit to activate the test unit and optionally conduct one or more blank value measurements and/or calibration measurements. Then, the test element is separated from the test unit to apply the body fluid sample, and the test element with the applied sample is reconnected to the test unit.

In view thereof, the test unit may be configured as a single-test-element test unit, where test elements are connected individually in series and may be manually connected to the test unit by inserting test elements successively into a test strip holder of the test unit from outside. Alternatively, the test unit may be configured as a multiple test element test unit, where the test unit has a test element cassette or magazine from which a plurality of test elements may be successively prepared. Accordingly, the methods described herein can be integrated into existing test units by programmatic modification of an analysis device.

As noted above, the test unit and test elements of the devices are configured to carry out an optically detectable detection reaction. As used herein, "optically detectable detection reaction" means any reaction whose course depends on or is at least influenced by the presence of the analyte to be detected, which may optionally include several component reactions and which is detectable by at least one optical measurement method. In some instance, the detection reaction can be a quantitative detection. For example, the term optical detectability may include detectability by means of a color change and/or by means of a color variation and/or by means of a fluorescence variation and/or by means of at least one variation in reflectivity, especially a variation in scattering reflectivity (i.e., a change in a reflectance value of the reagent element and especially of the reagent element field).

As used herein, "reflectance" means a diffuse (i.e., undirected) reflection of light in the ultraviolet and/or visible and/or infrared spectral region. Reflectance may be indicated in arbitrary units as a signal from the reflector of, for example, a LED, which receives the diffusely reflected light. Reflectance also may be indicated as relative reflectance in percent (shown in the following as % rR), where a change in any reflectance of the aforementioned detector signal may be taken as a ratio to a start value before completion of the detection reaction. In this manner, changes in reflectance, which are caused by changes and/or modifications in color, may be indicated in % rR. In general, reflectance may be indicated in arbitrary units, absolute units or relative units, which are generally included in the term reflectance.

Alternatively or additionally, however, other optical measurement variables may be used with respect to reflectance such as, for example, analog or digital electrical signals of optical detectors, fluorescence measurement values or similar optical measurement variables.

Devices incorporating the inventive concept also can include a data storage medium such as, for example, a volatile or non-volatile data storage medium on which a program structure is stored, and by means of which a method as described herein or portions thereof may be carried out by a computer or computer network after the program structure is loaded into the working memory of the computer or computer network.

Devices incorporating the inventive concept further can include a computer or computer network configured so as to wholly or partially carry out a method as described herein. In this manner, the computer or the computer network can include at least one microprocessor for carrying out the method or portions thereof.

Methods

Methods incorporating the inventive concept can include corresponding steps for determining an analyte concentration for at least one analyte even when a disturbance variable is present in a body fluid sample. The methods can include the steps described below, and these steps may, but not necessarily, be carried out in the sequence shown. Other sequences also are conceivable. Moreover, individual or multiple steps may be carried out either in parallel and/or overlapping in time and/or individually or in multiple repeated steps. Furthermore, the methods may include additional, unspecified steps.

The methods generally being with a step of applying a body fluid sample to a test element as described herein. In some instances, the body fluid sample is blood, particularly a blood droplet. The body fluid sample can be applied to the test element at at least one sample receiving site. In some instances, the applying step occurs at a sample receiving site configured as an opening of a capillary element in the test element, especially when the test element is in the form of a test strip. The sample receiving site can be on a side of the test element opposite to a detection surface of a reagent element field, so that the test element has an application side and a detection side, with the detection surface being opposite to the application side. The body fluid sample can be automatically or manually applied to the test element.

The methods also can include a step of detecting/measuring/monitoring a time course of at least one measurement variable, where a change in the reagent element (e.g., the stable coenzyme) due to reaction with the analyte of interest may be detected in any manner using the at least one optical measurement variable. In this case, all known methods in the art may be used, such as methods of detecting enzymatic reactions. As used herein, "optical measurement variable" means a quantitatively determinable variable and/or a quantitatively determinable signal based on using one or more optical measurement methods.

In particular, the optical measurement variable may be a measurement variable that is detected by means of a reflectance measurement and/or a scattering reflection on the reagent element on a test field surface of a test field including the reagent element. Accordingly, the optical measurement variable may include at least one reflectance value of the reagent element that can be determined at one or more wavelengths.

In some instances, the detection methods are optical detection methods that include, but are not limited to, measuring reflection and/or reflectance, absorption, fluorescence, circular dichroism (CD), optical rotatory dispersion (ORD), refractometry, etc. In other instances, the optical detection method is photometry.

For photometric measurement of a change in the reagent element caused by conversion with the analyte, at least one mediator may be used in the reagent element, and the mediator may increase the reactivity of the reduced coenzyme and can allow or facilitate a transfer of electrons onto a suitable optical indicator and/or a suitable optical indicator system. Alternatively, however, direct detection without the presence of a mediator may be carried out.

As used herein, "time course of the at least one optical measurement variable" means a quantitative detection of the at least one optical measurement variable at different time points (e.g., at 2, 3, 4, 5 or more time points) and/or continuous detection of the optical measurement variable as a function of time. For example, the determined time course may include a function in which respective optical measurement variables of the reagent element that have been determined are continuously or discontinuously assigned to the relevant measurement times at which these optical measurement variables were determined. This assignment may be carried out in the form of a table, a matrix and/or in the form of a continuous function. For example, the time course may be determined as a curve on which the respective optical measurement variables are assigned to the respective measurement times. The time course may be stored in a volatile and/or non-volatile data storage unit of the device used in the methods.

As used herein, "time" means any variable that can characterize a progression of the methods. Time may be indicated in units of an actual time, for example in seconds, corresponding to an actual clock. Alternatively or additionally, time may be indicated in other units such as, for example, corresponding to an internal "clock" of a measuring unit of the devices used in the methods. This "clock" may include a regular sequence of clock cycles.

The at least one variable used for characterizing the time may be correlated linearly with a real time and/or a flow of real time on an actual clock. In general, the time may be indicated as absolute time such as, for example, as an absolute time point. Alternatively or additionally, time may be indicated on a relative basis such as, for example, as time beginning from a particular event and/or start time.

The time course of the at least one optical measurement variable may include a quantity of data in which respective measurement values are assigned to relevant measurement times of the at least one optical measurement variable at which the optical measurement variables were determined.

In the methods, it is proposed that the determined time course of the at least one optical measurement variable be subdivided into at least two time intervals of the time course of the optical measurement variable. These at least two time intervals may be wholly or partially different and independent of each other, so that these at least two time intervals do not overlap. As used herein, "time interval" means a quantity of measurement times where the quantity includes the at least two measurement times, respectively, at which at least one optical measurement variable each was determined. For example, the time interval may include an infinite quantity with at least two measurement times. Alternatively, the time interval may be arranged in such a manner that no discrete measurement times are included, but optical measurement variables are determined during the time interval in a wholly or partially continuous manner, ultimately giving rise to an infinite quantity of measurement times. Alternatively still, the quantity of measurement times may include a measurement interval that is closed, closed at one end, or open.

To determine the disturbance variable value based on the time course of the optical measurement variable during the first time interval, at least one characteristic variable may be determined from the time course of the optical measurement variable during the first time interval. The first time interval may be selected such that the sudden wetting-induced change lies wholly or at least partially within the first time interval. As explained above, this characteristic variable may be a change in a reflectance value during a sudden wetting-induced change or during a portion of the sudden wetting-induced change. Here and in the following, no further distinction is made between the terms reflectance and reflectance value.

As used herein, "a sudden wetting-induced change" means a sudden change in at least one optical measurement variable that is attributable to wetting of the reagent element with the body fluid sample such as a blood sample. In particular, the sudden change may be such that at least one optical measurement variable changes due to wetting of the reagent element with the sample by at least about 1%, by at least about 2%, by at least about 5%, by at least about 10%, by at least about 15%, or even by at least about 20%.

The sudden wetting-induced change generally is such that wetting with the body fluid sample such as blood causes the at least one optical measurement variable to change suddenly from a start value recorded prior to wetting of the reagent element with the sample to an end value after wetting of the reagent element with the sample, where after the end value is reached, a further, more gradual change in the at least one optical measurement variable may occur due to reaction of the sample or sample components with the reagent element. The occurrence of the sudden change in at least one optical measurement variable itself can be characterized as a sudden wetting-induced change. A difference between the end value and the start value or an amount of this difference also may be characterized per se as a sudden wetting-induced change.

A beginning of the sudden wetting-induced change, which also is referred to as the wetting time point, may be recognized by comparing the optical measurement variable or a change therein with at least one threshold value. For example, the optical measurement variable may be determined at at least one first wavelength, and the wetting time point and/or the beginning of the sudden wetting-induced change may be determined based on a major change in the optical measurement variable after the body fluid sample to the test element, the reagent element of which is reached and/or wetted by the sample.

It may be concluded that the sudden wetting-induced change has begun if the optical measurement variable undergoes a temporal change that corresponds to at least one preset threshold value and/or exceeds a preset threshold value. For example, the at least one optical measurement variable may be compared with the at least one preset threshold value immediately or after being processed. The processing may include filtering and/or smoothing of the at least one optical measurement variable filtering through a low-pass filter and/or a smoothing by averaging over preset time intervals and/or data reduction. In this manner, in comparing the at least one optical measurement variable with the at least one preset threshold value, background noise and/or short-term artifacts can be ignored. For example, if a reflectance value of the reagent element and/or of a test field containing the reagent element is determined as an optical measurement variable, a wetting time point may be detected if the reflectance value changes by more than one preset threshold value within a period of, for example, 1 sec, that is, by more than about 0.1% to about 10%, or alternatively by more than about 1% to about 5%. In general, threshold values for recognizing the wetting time point can be from about 0.1% to about 20%, or alternatively from about 0.1% to about 10%. Other threshold values, such as higher threshold values, are also suitable in principle.

The end of the sudden wetting-induced change, which also is referred to as the end time point, may be determined by comparing the at least one optical measurement variable or a change therein such as a temporal change with at least one threshold value.

It may be concluded that the end of the sudden wetting-induced change has been reached if a temporal change in the at least one optical measurement variable reaches or exceeds a further preset threshold value after prior determination of higher changes over time. If it is found that after prior recognition of the beginning of the sudden wetting-induced change, the change in reflectance over time drops below a preset threshold value, it may be concluded that the end of the sudden wetting-induced change has been reached. For example, change rates of about 0.1% to about 10%, or alternatively of about 1% to about 5% reflectance per second may be set as threshold values. The time point at which the rate of change drops below the preset threshold value may be recognized as the end time point, even if a subsequent more gradual change in reflectance (i.e., with lower change rates) is still possible.

In such cases, a difference between reflectance at the wetting time point and reflectance at the end time point may be used as a characteristic variable for sudden wetting-induced change. Other characteristic variables indicative of the sudden wetting-induced change may alternatively or additionally be used.

To determine the at least one disturbance variable value from the characteristic variable, one may use a preset and/or determinable relation between the characteristic variable and the disturbance variable. For example, as described in detail below by way of example, a relation between a change in reflectance during a sudden wetting-induced change and the disturbance variable (e.g., Hct in the blood) may be empirically determined and stored in, for example, a data processing unit and/or a data storage unit of a test unit. In this manner, the correlation may be determined by means of simple measurements in which the disturbance variable is determined by a different method (i.e., by classical detection of hematocrit) and in which the respectively relevant characteristic variable is derived from the first time interval of the time course of the optical measurement variable and assigned to this value of the disturbance variable. A table, in particular an electronic table, therefore may be prepared in which respective characteristic variables are assigned to disturbance variables or vice versa.

Alternatively or additionally to ascertaining one or more characteristic variables from the first time interval of the time course of the optical measurement variable, other methods for determining the disturbance variable from the first time interval of the time course of the optical measurement variable are possible. For example, at least one pattern recognition method may be used to evaluate the first time interval of the time course. In this manner, the first time interval of the time course of the optical measurement variable may be compared with one or more comparison patterns, and according to this comparison, the disturbance variable may be determined.

In some instances, several comparison patterns may be stored in a test unit, where it is known that each comparison pattern is to be assigned to a certain disturbance variable based on empirical measurements. These comparison patterns may be compared sequentially or simultaneously, with the time course of the optical measurement variable in the first time interval by one or more correlation methods and/or pattern comparison methods generally known in the art. In accordance with the result of this comparison, the most suitable comparison pattern for the time course of the optical measurement variable during the first time interval may be selected, and the disturbance variable corresponding to this comparison pattern may be used.

Alternatively or additionally to a pattern comparison of the time course of the optical measurement variable during the first time interval, an analytical evaluation of the time course of the optical measurement variable during the first time interval may be conducted to determine the disturbance variable by means of this analytical evaluation. For example, one or more adaptation functions (fit functions) may be preset, with one or more parameters to be adapted, where the adaptation function is adapted to the time course of the optical measurement variable during the first time interval. For this purpose, the method of least squares may be used, although other adaptation methods also are conceivable.

In accordance with the adaptation function determined by this method, based on the one or more adaptation parameters thus determined, the disturbance may then be determined. For example, one or more tables in which the respective relevant disturbance variables for one or more adaptation parameters are deposited may be preset or determinable. As such, during a sudden wetting-induced change, adaptation of the time course of the optical measurement variable in the first time interval may be carried out using an exponential function, which may also have an offset, and the disturbance variable (e.g., Hct value) may be determined based on the adapted parameters of the exponential function.

At least one second time interval of the time course of the optical measurement variable is used to determine the analyte concentration to be detected. In this case, in the second time interval, the time course of the same optical measurement variable used during the first time interval for determining the disturbance variable is observed. In particular, an optical measurement variable may be used that is determined at the same wavelength as the optical measurement variable during the first time interval. Methods also are conceivable in which, during the first time interval and the second time interval, different optical measurement variables for determining the disturbance variable and/or for determining the analyte concentration are used.

During the second time interval, the analyte concentration is determined from the time course of the optical measurement variable. Specifically, a change in the optical measurement variable in the second time interval may be determined, where for determining the analyte concentration, one uses the optical measurement variable at a time point that can also be referred to as the end time point and at which the detection reaction is essentially completed. In particular, the time point at which the optical measurement variable is determined and used for determining the analyte concentration may be selected in such a manner that at the time point, the temporal change in the optical measurement variable is below a preset threshold value.

For this purpose, a preset and/or known and/or determinable correlation between the time course of the optical measurement variable during the second time interval and the analyte concentration may be used. This type of correlation may again, for example, be analytically and/or empirically and/or semi-empirically determinable. As described above, this correlation may exist in that based on the time course of the optical measurement variable during the second time interval, at least one characteristic variable is determined, which can be referred to as the second characteristic variable (in contrast to the above-described characteristic variable that can be used to determine the disturbance variable). This second characteristic variable also can be referred to in the following as a "further" characteristic variable. The term "second" or "further" characteristic variable is used in this case regardless of whether or not a first characteristic variable is present and is understood purely as a designation.

This second characteristic variable may be at least one optical measurement variable during the second time interval, which was determined at one or more preset, predefined, or at least determinable and/or defined time points within the second time interval. Alternatively or additionally, the further characteristic variable may include at least one optical measurement variable that was determined at at least one measurement time within the second time interval when the time course of the optical measurement variables was no longer changing or essentially no longer changing. For example, the time course of the optical measurement variable in the second time interval may be monitored, and rates of change in the optical measurement variables could be detected. If the rate of change (e.g., the change in the optical measurement variables) remains within a preset time period of time below a preset threshold, it may be determined that the time course of the optical measurement variable is essentially no longer changing. It may be predetermined that a relative reflectance value is not to change by more than about 0.1% to about 10% per second, or by not more than about 1% to about 5% per second, or even by not more than about 2% per second, so that the time course of the reflectance value will essentially no longer change according to specifications.

If this condition is met, a subsequently detected optical measurement value may be used as a further characteristic variable. This further characteristic variable then may be used to determine the analyte concentration by converting this characteristic variable, in particular an optical measurement value, into an analyte concentration in the blood by means of a corresponding preset, known or determinable correlation. Such conversion methods are known in principle, as reflectance values are already converted to corresponding glucose concentrations on conventional blood glucose meters.

Alternatively or additionally, similarly to evaluation of the first time interval, other methods may be considered in using one or more characteristic variables to evaluate the time course of the optical measurement variable during the second time interval as well. For example, similarly to the above description of the first time interval, one or more pattern comparisons and/or an adaptation of one or more adaptation functions to the time course may be carried out during the second time interval.

An analyte concentration may again be determined by comparison with a plurality of deposited patterns, and/or adaptation parameters determined for one or more adaptation functions such as, for example, exponential functions with and/or without offset, may be used to determine the analyte concentration. As is the case during evaluation of the first time interval, during evaluation of the second time interval one may use for this purpose a data processing unit such as a microcomputer that is a component of a test unit used in the method, for example in an analysis device of a test unit.

In summary, to detect the optical measurement variable in the first time interval and in the second time interval, the reagent element may be irradiated respectively with at least one interrogating light beam using at least one interrogating light source. Furthermore, at least one of the response light beam(s) emitted by the reagent element may be determined by means of at least one detector. Specifically, in the first time interval, the reagent element may be irradiated with at least one first interrogating light beam emitted by at least one first interrogating light source, and at least one first response light beam emitted by the reagent element may be detected by means of at least one first detector. Correspondingly, during the second time interval, the reagent element may be irradiated with at least one second interrogating light beam emitted by at least one second interrogating light source, and at least one second response light beam from the reagent element may be detected by means of at least one second detector. In this case, the first interrogating light source may identical to or different from the second interrogating light source. The first detector may be configured so as to be identical to or different from the second detector. The interrogating light beam and the response light beam may in the first time interval and/or the second time interval respectively show the same wavelength and/or different wavelengths. Specifically, the first interrogating light beam during the first time interval may show the same wavelength as the first response light beam during the first time interval. Moreover, during the second time interval, the second interrogating light beam may have the same wavelength as the second response light beam. Furthermore, the first interrogating light beam and the second interrogating light beam may have the same wavelength or different wavelengths. Likewise, the first response light beam and the second response light beam may have the same wavelength or different wavelengths.

In some instances, the interrogating light beams in the first time interval and the second time interval show the same wavelength and/or the same spectral properties. This may mean that the optical measurement values during the first time interval and the second time interval are determined at the same wavelength or wavelengths. For example, the interrogating light beams in the first time interval and the second time interval may be produced by the same light source by one or more LEDs. Moreover, the response light beams may show the same wavelength and/or the same spectral properties in the first time interval and the second time interval. As used herein, "spectral properties" means a spectral composition and/or intensity course of the response light beams as a function of the wavelength or frequency, which can be standardized or can be determined as a relative intensity course. Specifically, although the response light beams in the first time interval and in the second time interval may in principle differ in their intensity and/or amplitude, the spectral composition and/or a standardized spectrum of the response light beams in the first time interval and the second time interval are identical or show a deviation (e.g., ascertained by means of a correlation function) of not more than about 20% or even not more than about 10%. In particular, detection of the at least one optical property in the first time interval and the second time interval may be conducted at the same wavelength and/or in the same wavelength range. In addition, detection of the response light beams during the first time interval and the second time interval may be carried out by means of the same detector.

The interrogating light beam in the first time interval and/or second time interval may in particular have a wavelength of about 635 nm, about 660 nm, about 770 nm, about 815 nm or even about 880 nm. However, other wavelengths may be used. In particular, the aforementioned wavelengths may be in the spectrum of the interrogating light beam, such as central wavelengths and/or peak wavelengths. Moreover, narrow-band light beams may be used as the interrogating light beams. Such narrow-band light beams have a spectral full width at half maximum (FWHM) of not more than about 50 nm, not more than about 40 nm, not more than about 30 nm, not more than about 20 nm, or even not more than about 10 nm. For these interrogating light beams, one may use beams from light sources with an FWHM from 5 nm to about 60 nm, or even from about 10 nm to about 20 nm, especially LEDs having the aforementioned spectral properties.

The methods described herein take into account that it not only is possible to determine the disturbance variable value but also is possible to determine the analyte concentration (i.e., a corrected and/or compensated analyte concentration). Thus, the methods also can include a step of correcting and/or compensating the analyte concentration in view of the disturbance variable value. For example, by means of the disturbance variable such as Hct, at least one correction can be determined (e.g., a correction function, a correction factor and/or a correction offset), where a corrected analyte concentration is determined from the second time interval taking into account the correction from the first time interval. In this case, the corrected analyte concentration may be determined subsequently, or also simultaneously with determination of the actual analyte concentration. Specifically, a raw analyte concentration may be determined from the time course of the optical measurement variable during the second time interval, which is then corrected using the correction determined for the disturbance. Alternatively or additionally, however, the correction may be taken into consideration during evaluation of the second time interval. Therefore, by taking the correction into account, a corrected analyte concentration can be derived directly from the time course of the optical measurement variable during the second time interval. This may be conducted by deriving a "second" characteristic variable from the time course of the optical measurement variable during the second time interval, which then is converted to a corrected analyte concentration using a known or determinable correlation, where the previously determined disturbance variable is incorporated into the correlation.

As used herein, "correction" means any manipulation, in particular any mathematical operation, that reduces, minimizes or completely eliminates the influence of the at least one disturbance variable on determination of the analyte concentration from the time course of the optical measurement variable during the second time interval, particularly in such a way that analyte concentrations determined are still comparable despite different degrees of interference by the disturbance variable. In particular, the correction may make it possible, even in the case of sharply differing values of the disturbance variable, to derive essentially the same analyte concentration from the time course of the optical measurement variable during the second time interval, if the actual analyte concentration is identical.

As used herein, "essentially the same" means a deviation in the analyte concentration determined in this manner of not more than about 10% or even not more than about 5%. For example, the correction may take place in such a way that at one and the same actual analyte concentration, in particular at one and the same actual blood glucose concentration, but with a Hct difference of about 10%, the corrected analyte concentrations, particularly the corrected blood glucose concentrations, deviate from one another by not more than about 10% or even by not more than about 5%.

In particular, the correction may be conducted in such a way that the corrected analyte concentration corresponds to a theoretical analyte concentration that would have been measured if the disturbance variable had been at a preset value at the time point of measurement. For example, a certain reference value of the disturbance variable may be preset, with the correction being conducted in such a way that the analyte concentration is converted to the analyte concentration at the reference value of the disturbance variable. For example, the corrected analyte concentration may constitute the analyte concentration at a reference value of 43% Hct.

Moreover, the correction may generally be deposited in the form of a correlation, table and/or in other form such as, for example, in a test unit, in an analysis device of a test unit, or in a data storage unit and/or data processing unit of an analysis device of a test unit. For example, the correction may be deposited in the form of one or more correction functions and/or one or more correction factors and/or one or more correction offsets, which may be a continuous function of the previously determined disturbance variable and/or may be determined by means of point-wise assignment in a table, especially an electronic table, corresponding to the determined disturbance variable. For example, a correction offset may be understood as an error contribution of the disturbance variable to the analyte concentration and/or to the optical measurement variable such as an additive or subtractive contribution.

Initially, determining the at least one disturbance variable may be conducted based on the time course of the optical measurement variable during the first time interval. After this, according to the disturbance variable, one may select the type of correction to be conducted, specifically using a correction factor and/or a correction offset and/or a correction function by selecting the correction factor and/or correction offset assigned to the relevant disturbance variable from a table and/or list. Moreover, according to the methods described herein, from the time course of the optical measurement variable during the second time interval, a raw analyte concentration may be determined. The raw analyte concentration then may be processed using the correction factor.

Possible approaches include multiplying the raw analyte concentration by the correction factor and/or increasing or decreasing the raw analyte concentration by the amount of the offset so that a corrected analyte concentration can be determined. Alternatively or additionally, correction may be immediately conducted on evaluation of the time course of the optical measurement variable during the second time interval. For example, one may first ascertain the first time interval from the disturbance variable. Next, by selecting from a list, a correlation may be selected by means of which the analyte concentration may be determined from the time course of the optical measurement variable during the second time interval, where the correlation already takes the disturbance variable into account, so that the analyte concentration obtained is already a corrected analyte concentration. During the second time interval, as described above, one or more reflectance values may be determined at an end time point of the detection reaction. This at least one reflectance value may be directly converted, while taking the disturbance value into consideration, into a corrected analyte concentration.

The correction may be previously determined and/or determinable and may be deposited in a test unit. In particular, empirical or semi-empirical methods may be used for determining the correction. For example, a measurement series may be conducted, by means of which corresponding correction factors and/or correction offsets and/or other kinds of correction functions may be determined. This series of experiments may be configured in such a way that body fluid samples are produced that have the same actual analyte concentration (e.g., the same actual glucose concentration) but show differing disturbance variable values (e.g., Hct).

The respective disturbance variable values of the individual samples may be determined independently by, for example, means of a known centrifugation method. If one wishes to determine the influence of other kinds of disturbance variables, these disturbance variables may be correspondingly determined as a rule by means of independent detection methods. The respective test strips may then be used to determine a raw value for the analyte concentration, and a correction factor and/or correction offset may be determined for each disturbance variable of the measurement series to convert the raw analyte concentration into the actual analyte concentration. This calibration or gauging constitutes only one of many empirical possibilities for determining corresponding corrections in an empirical or semi-empirical manner. Theoretical models for influencing the disturbance variable also may be used in principle to determine a correction. The empirically or semi-empirically determined corrections arrived at may be deposited in a table and/or matrix and/or list in a data storage unit and/or a data processing unit of an analysis device of a test unit. For example, the data storage unit may comprise a volatile and/or a non-volatile data storage unit. Specifically, the data storage unit may include an EEPROM. Alternatively or additionally, for depositing the corrections in a data storage unit and/or data processing unit of an analysis device of a test unit, one or more of the aforementioned corrections may also be read in via the test unit using at least one interface such as, for example, a hard-wired and/or wireless interface. One or more corrections also may be stored in an external unit and/or external data storage unit and transferred to the test unit. For example, at least one so-called ROM key may be used as an external data storage unit that contains one or more corrections in stored form and can be connected to an interface of the test unit for the purpose of data transmission. Alternatively or additionally, one or more corrections may also be stored on an RFID chip as an external data storage unit, so that at least one correction can be transmitted by radio to the test unit. Alternatively or additionally, at least one data transmission network may be used to transfer at least one correction to the test unit, such as the Internet and/or a wireless telecommunications network.

As explained above, the correction may include dependency of the optical measurement variable on the disturbance variable, particularly a correlation between a reflectance value of the reagent element and a disturbance variable value.

SUMMARY

In contrast to known static measuring methods, methods therefore are provided herein in which a time course of an optical measurement variable of the reagent element is determined and subdivided into at least two time intervals, where both the disturbance variable and the analyte concentration are determined from the time course, albeit in different time intervals. The methods take into account the inventors' observation that the disturbance variable and the analyte concentration in different time intervals may influence the time course of the optical measurement variable. Thus, a disturbance variable such as the concentration of the disturbance variable (i.e., a Hct value) ordinarily manifests itself primarily in an initial period of the first time interval of the time course of a reflectance value, specifically in the form of an initial sudden wetting-induced change. In this initial time interval, however, when Hct and/or another kind of disturbance variable can be variably derived from the time course of the optical measurement variable, the detection reaction that allows a conclusion to be drawn on the analyte concentration ordinarily is not completed or completed only to a minor extent when more than about 20%, not more than about 10%, or even not more than about 5% of the total possible reaction conversion has taken place. At a later time point, during the second time interval, the detection reaction is completed or largely completed to at least about 80%, to at least about 90%, or even to at least about 95%, so that the optical measurement variable can be used to detect an optically detectable change in the reagent element, which can then in turn be used to determine the analyte concentration.

For example, within the first time interval, the change in the at least one optical measurement variable may essentially be attributable to physical processes (e.g., to solvating processes and/or diffusion processes). Consequently, the first time interval may be selected in such a way that during this first time interval, no or only negligible conversion of the reagent element and/or no or only a negligible course of the detection reaction are observed such as, for example, conversion of about 5% or less, or even no enzymatic conversion. In the second time interval, on the other hand, the at least one optical measurement variable may essentially or additionally be determined by the analytical detection reaction of the reagent element. In this case, the course of the detection reaction, such as enzyme conversion, may be determined by the analyte concentration to be detected, such as glucose in the blood. The conversion of the reagent element and/or an active component of the reagent element may be considerably higher than the aforementioned percentages such as, for example higher than about 5%.

This possibility of temporal separation of the time course of the optical measurement variable into several time intervals that are influenced differently by the disturbance variable and the analyte concentration makes it possible to determine the disturbance variable and the analyte concentration from one and the same optical measurement variable. In contrast to one-time statistical measurements, however, evaluation of the time course of the optical measurement variable allows reduced equipment expenses and favorable precision in determining the disturbance variable and the analyte concentration. Alternatively or additionally to the above-described spectral separation of the measurements of the disturbance variable and the analyte concentration, temporal separation of determination of the disturbance variable and the analyte concentration can take place according to the invention by subdividing the time course into the first time interval and the second time interval.

In this respect, it is generally to be noted that this subdivision may be carried out wholly or partially. In particular, the first time interval and the second time interval respectively may constitute a cohesive quantity of successive measurement times to which the respective measurement values of the optical measurement variables are assigned. The first time interval may in particular be wholly or partially set prior to the second time interval. A time gap may be arranged between the first time interval and the second time interval. Alternatively, however, the first time interval and the second time interval may at least partially overlap.

The first time interval may begin at the start of a measurement (e.g., on start-up of a test unit used to carry out the method). Alternatively, the first time interval may also start when the beginning of a sudden wetting-induced change in the course of the optical measurement variable is recognized by observation of a sharp change in the optical measurement variable over time, which before this may be approximately constant. For example, this beginning of the sudden wetting-induced change may be detected by comparing the optical measurement variable with a threshold value. When the change in the optical measurement over time first exceeds this threshold value, it may be concluded that the sudden wetting-induced change has begun, and the respective time point may be selected as the start time of the first time interval.

Likewise, the end of a sudden wetting-induced change may be used as the end of the first time interval. The time course of the optical measurement variable (e.g., reflectance) ordinarily shows a kink at the end of the sudden wetting-induced change, which can be recognized in a discontinuity of the first derivative of the time course. This kink can be explained by the fact that during the sudden wetting-induced change, the optical measurement variable is predominantly influenced by wetting of the reagent element with the body fluid sample such as blood or blood components. Subsequently, the optical measurement variable is then influenced by the course of the detection reaction and the change in at least one optically detectable property of the reagent caused thereby. The above-described kink point ordinarily forms at the transition between the two areas. It is therefore possible to determine the time point of the kink by comparing the optical measurement variable and/or a derivative of the time course of the optical measurement variable and select it as the end time point for the first time interval. At the same time, the time point at which this kink occurs may be selected as the start time for the second time interval.

As the end time point for the second time interval, one then may select a time point at which the time course of the optical measurement variable no longer changes or essentially no longer changes according to the above-described threshold value condition, according to which, within a preset time interval, the optical measurement variable may change only by a maximum preset threshold value or by less than a preset threshold value.

Advantageously, the selection of the first time interval and the second time interval may be conducted subsequently during evaluation of the time course of the optical measurement variable, which in particular can be carried out using at least one data processing unit. Moreover, the methods described herein may be easily automated, so that during an evaluation of the time course of the optical measurement variable, one may automatically set the start time of the first time interval as the time point of the start of a sudden wetting-induced change, the end of the sudden wetting-induced change as the end time point of the first time interval and the start of the second time interval, and a time point at which the optical measurement variable essentially no longer changes as the end time point of the second time interval.

After this division of the time course of the optical measurement variable has been conducted, one can use the data processing unit of the devices to determine the disturbance variable and the analyte concentration according to one or more of the algorithms described herein, based on the time courses during the first time interval and the second time interval. As a characteristic variable during the first time interval, one may select a difference between the optical measurement variable at the start time of the first time interval and the optical measurement variable at the end time point of the first time interval such as, for example, a change in the optical measurement variable during the first time interval. This determination of the characteristic variable for determining the disturbance variable in the body fluid sample, especially Hct, can easily be automated and thus can easily be carried out by a data processing unit. As an example of a second characteristic variable for determining the analyte concentration from the second time interval of the time course of the optical measurement, one may use an optical measurement variable at a time point that shows a preset time gap from a start time of the second time interval and/or at which the time course of the optical measurement variable essentially no longer changes.

The methods described herein may be developed in various ways. As described above, the first time interval may in particular be an initial time interval of the time course of the optical measurement variable. This initial time interval may begin with applying the body fluid sample to the test element and/or with switching on of a test unit and/or with a recognition of the start of a sudden wetting-induced change in the time course. Other start times are also possible. The second time interval may in particular be subsequent to the first time interval.

The time course of the optical measurement variable in the first time interval may specifically occur in response to the sudden wetting-induced change in the optical measurement variable. The sudden wetting-induced change often is due solely to the fact that a dry reagent element shows a different value of the optical measurement variable from a reagent element wetted with body fluid sample (i.e., a "wet" reagent element). As wetting can be strongly influenced by the disturbance variable, it is possible to at least and/or at least approximately determine the disturbance variable based on the sudden wetting-induced change. The sudden wetting-induced change can be caused in particular by wetting of the reagent element with the body fluid sample before the optically detectable detection reaction is completed to a significant extent.

As explained above, the at least one optical measurement variable and the time course thereof during the first time interval and the second time interval may be determined in particular at the same wavelength. In general, the optical measurement variable may be determined at at least one first wavelength, where the wetting time point and/or start of a sudden wetting-induced change may be determined from a major change in the optical measurement variable after applying the body fluid sample to the test element, the reagent element of which is reached and/or wetted. As used herein, "major change in the optical measurement variable" means a change that corresponds to at least one preset threshold value and/or exceeds more than one preset threshold value. The at least one optical measurement variable may be compared directly or after a processing step to the at least one preset threshold value. For example, the processing step may include filtering and/or smoothing of the at least one optical measurement variable (e.g., filtering through a low-pass filter and/or a smoothing by averaging over preset time intervals) and/or data reduction. In this manner, by comparing the at least one optical measurement variable with the at least one preset threshold value, background noise and/or short-term artifacts can be ignored. For example, if a reflectance value of the reagent element and/or of a test field containing the reagent element is determined as an optical measurement variable, a threshold value of about 1% to about 10% change in reflectance may be preset, such as about 7% to about 8%. Therefore, if a change in reflectance at the first wavelength is above this threshold value, one may conclude that the reagent element has been wetted with the body fluid sample (i.e., determine a wetting time point) and thus conclude that a sudden wetting-induced change has begun.

As described above, a wetting time point and thus a start of the sudden wetting-induced change may be determined in this manner. Specifically, this time point may be selected as the start time of the first time interval. The first time interval and the second time interval may be at least partially subsequent to the wetting time point. In some instances, the optical measurement variable in the first time interval may be determined with the second time interval at at least one second wavelength, where the second wavelength may be the same as the first wavelength.

The methods described herein may be carried out wholly or partially using a computer and/or a computer network and/or a computer program. In some instances, a computer program configured so as to wholly or partially carry out at least one method described herein after being loaded into the working memory of a computer or processor or computer network. In particular, detecting the time course of the at least one optical measurement variable of the reagent element may be wholly or partially carried out on a computer-implemented or computer-supported basis. Alternatively or additionally, the process step in which the at least one disturbance variable in the body fluid sample is determined from the at least one first time interval of the time course of the optical measurement variable may be wholly or partially carried out on a computer-implemented or computer-supported basis. Alternatively or additionally, the process step in which the analyte concentration is determined from the at least one second time interval of the time course may be wholly or partially carried out on a computer-implemented or computer-supported basis. Alternatively or additionally, combinations of the aforementioned process steps and/or other process steps may also be carried out by the computer program.

In some instances, the proposed computer program may be run on an analysis device of a device described as described herein. Correspondingly, the evaluation device may be programmatically configured to run the proposed computer program. For example, the evaluation device may comprise at least one data processing unit for running the computer program when the computer program is loaded into the evaluation device or the data processing unit. The data processing unit may include, for example, a microprocessor. Alternatively or additionally to running on the evaluation device, the computer program may also be wholly or partially run on another kind of computer or computer network. For example, this may be a physician's computer and/or a patient's computer. The evaluation also may take place in a manner that is wholly or partially separate from measurement. Specifically, the measurement data (i.e. the time course of the at least one optical measurement variable) may be loaded into the computer into a volatile or non-volatile storage device of the computer. An evaluation may be subsequently or simultaneously conducted by running the proposed computer program.

EXEMPLARY EMBODIMENTS

The inventive concept will be more fully understood upon consideration of the following non-limiting examples, which are offered for purposes of illustration, not limitation.

FIG. 1 shows an embodiment of a device 110 for determining a concentration of an analyte in a body fluid such as, for example, blood glucose concentration. The device 110 includes a test unit 112, which can be configured as a manual unit, and a test element 114 such as a test strip 116. The test unit 112 can include a test element holder 118 in which the test element 114 is held and can be moved into an application position (shown in FIG. 1). In the application position, a body fluid sample 120, such as a droplet of blood, can be applied to an application site 122 on the test element 114.

Generally, the test element 114 includes a reagent element 124, which may be a component of a reagent element field 126.

The device 110 also includes an optical detection device 128, by means of which at least one optical measurement variable of the reagent element 124 and in particular a time course of the optical measurement variable can be detected. For this purpose, the optical detection device 128 may have at least one light source 130 for producing at least one interrogating light beam 132 and at least one detector 134 for detecting at least one response light beam 136, where the response light beam 136 may be an interrogating light scattered or diffusely reflected by the reagent element 124. Further possible details on the optical detection device 128 will be discussed in greater detail below.

The device also can include at least one evaluation device 138. The evaluation device 138 may be connected unidirectionally or bidirectionally via at least one data line 140 to the optical detection device 128 and/or also may be fully or partially combined with the optical detection device 128 by, for example, fully or partially integrating the evaluation device 138 into the optical detection device 128. Other embodiments also are possible such as, for example, peripheral embodiments. The evaluation device 138 may include at least one data processing unit 142 such as, for example, a microcomputer. The data processing unit 142 may be programmatically configured so as to control and/or evaluate a program sequence/method as described herein for determining a concentration of at least one analyte in a body fluid sample 120. In addition, the evaluation device 138 can include at least one volatile and/or at least one non-volatile data storage unit 144.

In addition to the above, the device 110 may include further elements and/or features, including elements and/or features that constitute an interface between a user of the device 110 and the device 110. Accordingly, one or more operating elements 146 such as one or more keys and/or one or more display elements 148 may be provided. The one or more operating elements 146 can be configured unidirectionally and bidirectionally with respect to the evaluation device 138. Furthermore, the device 110 optionally can include one or more further interfaces such as, for example, one or more data interfaces by which data may be exchanged between the device 110 and one or more further devices such as measurement data and/or measurement results.

Figure 2:
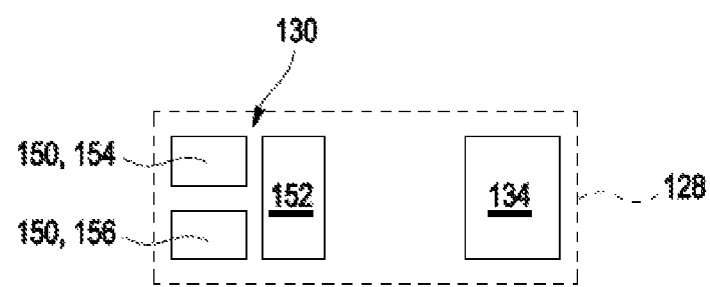
FIG. 2 shows a schematic representation of an optical detection device in plan view.

FIG. 2 shows a plan view of an embodiment of an optical detection device 128. The optical detection device 128 includes at least one interrogating light source 130 and at least one detector 134. These elements as a whole may be configured in particular with a semiconductor component. The interrogating light source 130 optionally includes at least one first LED (LED 1) 150 and at least one second LED (LED 2) 152. As shown in FIG. 2, the first LED also may be configured with multiple parts and includes transversely to a longitudinal extension direction of the test element 114, a first LED A 154 (LED1A) and a first LED B 156 (LED1B). This multicomponent embodiment of the first LED 150 may be used to provide better coverage of the reagent element field 126 with interrogating light. The first LED 150 can emit light at 660 nm and can be used for ascertaining a reflectance value to determine the analyte concentration. The second LED 152 can emit light at 880 nm and can be used for recognizing a start of a sudden wetting-induced change. The interrogating light 132 emitted by the reagent element field 126 by reflectance (i.e., diffuse scattering in the form of the response light beam 136) is detected by a detector 134 of a photodiode.

Figure 3:
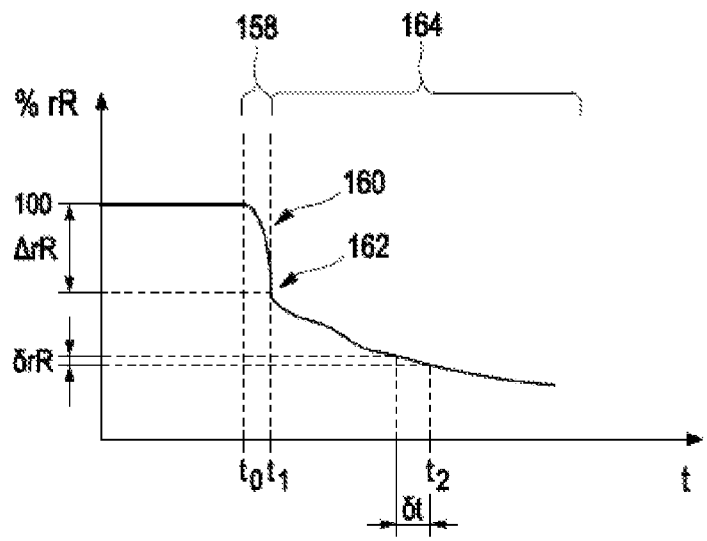
FIG. 3 shows a schematic representation of a time course of relative reflectance and subdivision into a first time interval and a second time interval.

FIG. 3 shows an embodiment of a time course of a signal typically detected by the detector 134 of an optical measurement value. The so-called relative reflectance (rR) is shown in FIG. 3 in percent as a function of time t.

As shown in FIG. 3, reflectance, before application of a body fluid sample 120, can be a so-called blank value, which is set arbitrarily to 100% relative reflectance and thus used as a reference value for subsequently detected signals.

After blood or blood components reach the reagent element 124, a wetting phase begins that is recognizable by the time course shown in FIG. 3. The wetting phase optionally can be recognized by means of the second LED 152. For example, the first LED 150 and the second LED diode 152 may alternately be switched on in a pulsed-intermittent operation. Alternatively or additionally, the beginning of the wetting phase may be determined by means of the first LED 150 so that a total of only one LED is required.

With the beginning of the wetting phase, the relative reflectance shown in FIG. 3 decreases sharply, which is designated as $t_0$. This time point may be recognized by means of a threshold value comparison with reflectance and/or by observing a change in reflectance.

Generally, the time point $t_0$ or an earlier time point than $t_0$ may be set as the start time point of a first time interval, which in FIG. 3 is indicated by the reference no. 158. The time point $t_0$ may be determined by comparing relative reflectance or a derivative of the time course of relative reflectance with at least one threshold value and/or by observing the derivative of the time course of relative reflectance such as, for example, automatically. As a rule, however, precise determination of the time point $t_0$ is not necessary, as relative reflectance hardly changes at all before the time point $t_0$, so that earlier time points than $t_0$ also may be used as the start time point of the first time interval 158. At time point $t_0$, a pronounced first kink ordinarily occurs. Beginning with the time point $t_0$, there is a decrease in relative reflectance by an amount $\Delta rR$, which also is referred to as a sudden wetting-induced change and is indicated in FIG. 3 by the reference no. 160.

At the end of the sudden wetting-induced change 160, and after relative reflectance has decreased by the amount $\Delta rR$, the time course of the relative reflectance generally shows a clear second kink 162. This second kink, which again can be automatically recognized by observing a derivative of the time course in FIG. 3 and/or by comparing the absolute values of relative reflectance and/or temporal change in relative reflectance with at least one preset threshold value, occurs at a time point indicated in FIG. 3 by $t_1$. The time point $t_1$, which characterizes the end of the sudden wetting-induced change 160, may be set as the end time point of the first time interval 158. At the same time, the time point $t_1$ may be set as the start time point of a second time interval indicated in FIG. 3 by the reference no. 164. While the first time interval of the time course is dominated by wetting effects of the reagent element 124, the second time interval 164 of the time course is dominated by progression of the optical detection reaction, which takes place within the reagent element 124. The second time interval 164 may be configured as an open interval and may include the entire time course for times $t \geq t_1$. Alternatively, the second time interval 164 may end at a preset time point such as, for example, at time point $t_2$ in FIG. 3. In general, it is noted that time intervals 158 and 164 may be configured as closed intervals, half-open intervals, or also as open time intervals.

In evaluating the time course of the optical measurement variable, which is shown as relative reflectance in FIG. 3, a disturbance variable such as hematocrit value is determined from the first time interval 158. For this purpose, one may observe a sudden change in reflectance that occurs during the sudden wetting-induced change 160 and is indicated as $\Delta rR$ in FIG. 3. This $\Delta rR$ may be used as a characteristic variable to determine the disturbance variable, particularly Hct, by using an algorithm as described in detail below. In contrast, the analyte concentration, particularly a glucose concentration, can be derived from the second time interval 164. This may take place in such a manner that at a fixed time point within the second time interval 164 a relative reflectance value rR is detected at a preset time after the time point $t_0$ or the time point $t_1$. The reflectance rR determined at this time may be used as a second characteristic variable from which the analyte concentration is determined. Alternatively or additionally, the time point $t_2$, at which reflectance is recorded to determine the analyte concentration may be taken as a so-called "end time point" and variably selected. As used herein, "end time point" means a time point at which the detection reaction is essentially fully completed. This essentially complete course of the detection reaction may be determined by verifying that the relative reflectance $\Delta rR$ does not change by more than a preset threshold value or less than a preset threshold value within a preset brief time interval $\Delta t$. By means of this threshold value determination, the end time point $t_2$ may be determined, and the reflectance rR at $t_2$ may be determined as a further characteristic variable or second characteristic variable for determining analyte concentration from the time course of the second time interval 164.

Figure 4:
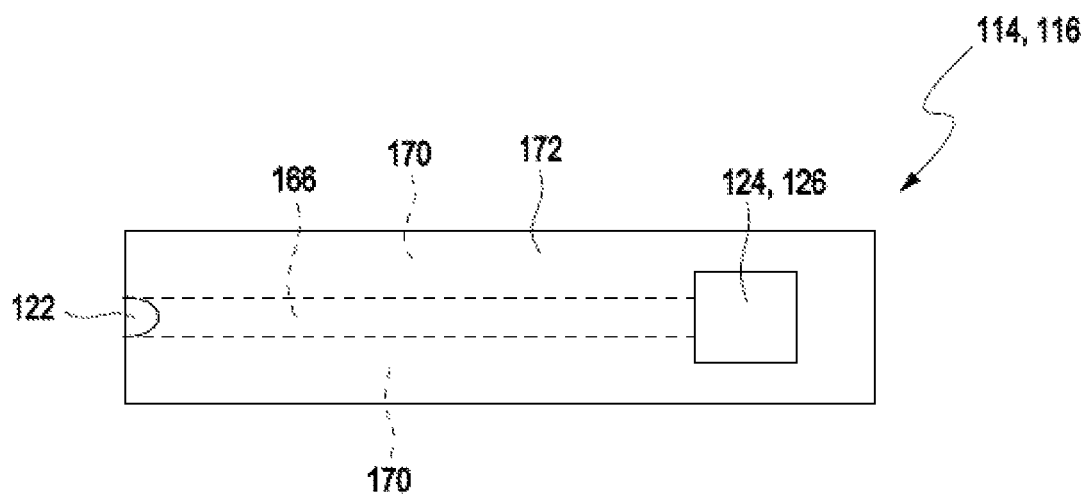
FIG. 4 shows a schematic representation of a test strip that can be used according to the invention in plan view.
Figure 5:
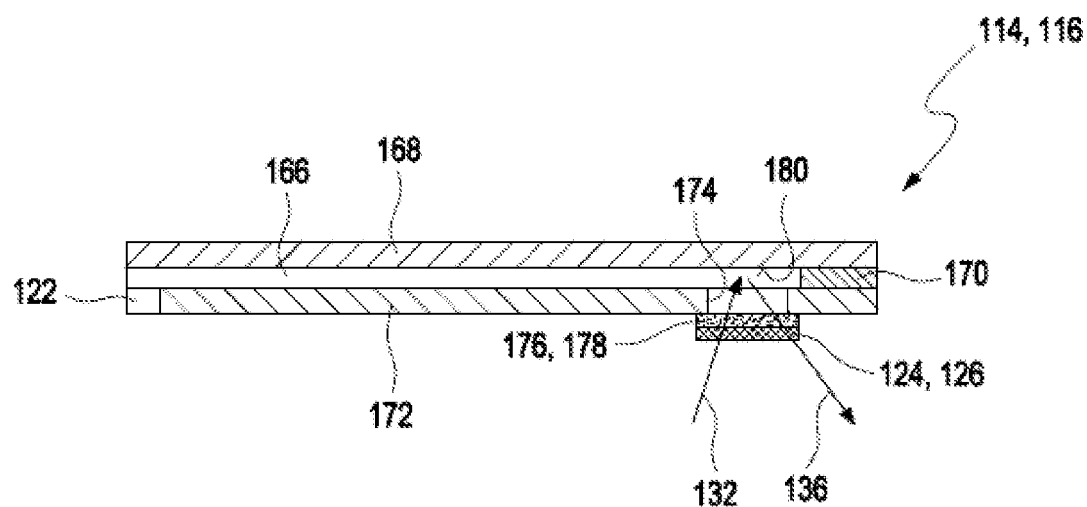
FIG. 5 shows a schematic sectional view according to FIG. 4.

FIGS. 4 and 5 show a plan view (FIG. 4) and a sectional view (FIG. 5) of an embodiment of a test element 114 in the form of a test strip 116 that can be used with the devices and methods described herein. The test strip 116 is configured as a capillary strip and includes a capillary element 166 indicated in FIG. 4 with a dotted line. The section level in FIG. 5 is selected to run longitudinally through the capillary element 166. The capillary element 166 is configured to transfer blood from an application site 122, at which the sample is applied, to the reagent element 124, in particular a reagent element field 126, by means of capillary forces. As shown in FIG. 5, the capillary element 166 may be configured, for example, as a layered structure in the test strip 116. For this purpose, the layered structure may include a carrier element 168 on which one or more distancing elements 170 (i.e., spacers) are placed. These spacers 170 are centrally distanced from one another so that the capillary element 166 is formed between the spacers 170. The spacers 170 are in turn covered by at least one covering film 172 that seals the capillary element 166. The covering film 172 can have an opening 174 provided (see FIG. 5) as a window. The opening 174 is covered by the reagent element field 126 with the reagent element 124; between the capillary element 166 and the reagent element field 126, at least one separating element 176 optionally may be provided as at least one separating layer 178. These elements are used to separate blood components such as red blood cells to keep them at least largely separate from the reagent element 124.

As shown in FIG. 5, the interrogating light beam 132 passes through the reagent element field 126 and optionally the separating layer 178. The interrogating light beam 132 optionally may be reflected and/or scattered directly on the reagent element 124 and/or on the separating element 176 and/or on a reflecting surface 180 of the carrier element 178. For this purpose, the carrier element 168 and/or the reflecting surface 180 may additionally show reflecting surfaces having reflecting properties by, for example, by configuring the carrier element 168 in white and/or mixing in white pigments such as titanium dioxide. If disturbance elements such as red blood cells accumulate in the separating layer 178 and/or at an interface between the separating layer 178 and the capillary element 166, these deposits will be penetrated at least twice in the case of the optical structure recognizable in FIG. 5, showing that optical detection can be influenced to a considerable degree by Hct. Hct correction therefore will contribute to a great extent to a considerable increase in detection accuracy in the case of structures according to FIGS. 4-5.

Figure 6:
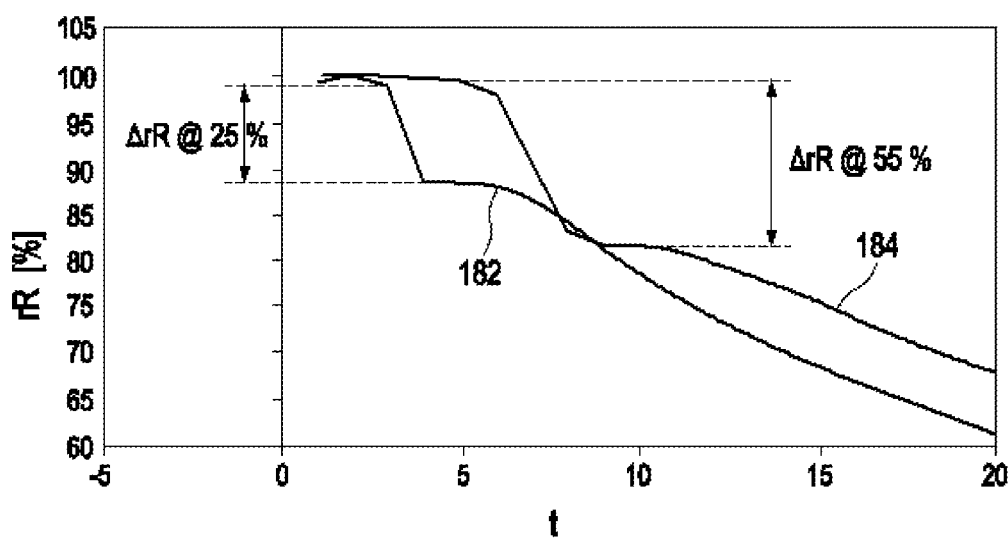
FIG. 6 shows time-course measurement of relative reflectance for two blood samples with different Hct values.

FIG. 6 shows an embodiment of a measurement method from which it can be recognized that a sudden change in reflectance during a first time interval 158 is indeed dependent on a Hct. This embodiment shows that for carrying out the method, it is not necessary to precisely determine the boundary points of the first time interval 158 and/or the second time interval 164. Relative reflectance rR values are analogous to the illustration in FIG. 3. The time t is shown in arbitrary units of clock time of a measurement (e.g., corresponding to an internal clock of the test unit 112 and/or the data processing unit 142). The time point at which the sample 120 was placed on the test element 114 was arbitrarily set as the zero point of the time.

As shown in FIG. 6, two measurement curves were obtained with different blood samples 120. Specifically, reference no. 182 shows a measurement of a blood sample 120 with a Hct value of 25%, and curve 184 shows a measurement of a blood sample 120 with a Hct value of 55%. The glucose content in both samples was selected so as to be equal. For the structure of the test elements 114 used and the reagent element 124, reference may be made for illustrative purposes to EP Patent Nos. 1035921, 1039298 and 0821234, as well as WO Patent Application Publication No. 2007/118647. See also, EP Patent Nos. 1035919 and 1035920.

The results in FIG. 6 show that the samples produce a different sudden wetting-induced change ΔrR. While the curve 182 shows a sudden wetting-induced change ΔrR of about 12%, the curve 184 shows a sudden wetting-induced change of about 20%.

Figure 7:
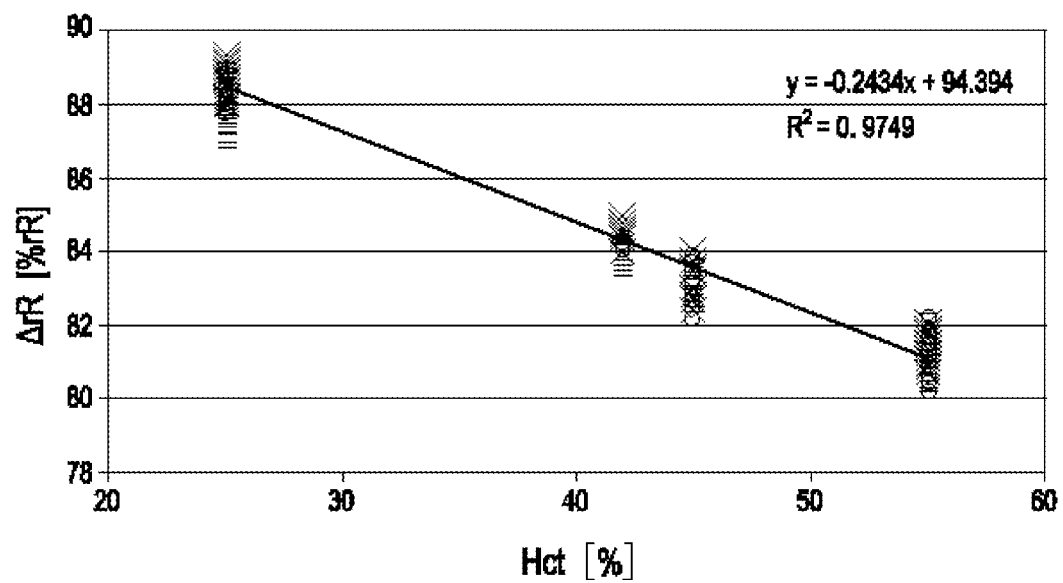
FIG. 7 shows a correlation between the extent of a sudden wetting-induced change and Hct value.

FIG. 7 shows systematic measurements of dependency of the change in reflectance ΔrR during the sudden wetting-induced change on Hct. 10 blood samples per Hct value were prepared with 50, 120 and 300 mg/dL of glucose, respectively, and evaluated. The different glucose concentrations are indicated in FIG. 7 with different symbols. In this case, the crosses denote concentrations of 50 mg/dL, the blank circles denote concentrations of 150 mg/dL, and the vertical lines indicate concentrations of 300 mg/dL glucose. The solid line is an adaptation through all of the measurement points, and its equation is indicated in FIG. 7 at the upper right.

The measurement results in FIG. 7 show that the sudden wetting-induced change ΔrR is dependent on Hct with a high degree of reproducibility. The dotted line and the indications in the upper right field of FIG. 7 show an arbitrary adaptation of a straight line to the measurement course of the points in FIG. 7. This shows that the dependency of the sudden wetting-induced change ΔrR on Hct value can be shown with good approximation in the form of a straight line.

Hct therefore may be determined according to the following formula based on a decrease in reflectance calculated with respect to the sudden wetting-induced change ΔRem (corresponding to ΔrR in FIG. 6):

$$Hct = a * \Delta Rem(\text{sudden wetting-induced change})^b + c \quad (1).$$

The terms a, b and c may be determined once for a specific reagent. For example, the terms a, b and c may be deposited in the data storage unit 144 of the data processing unit 142 and/or processed in a different manner (e.g., they may be ascertained, as stated above, as corrections on the device 110 and/or the test unit 112 via at least one interface and/or by means of at least one ROM key and/or by means of at least one RFID chip). Alternatively or additionally, the aforementioned terms may be adjusted after testing and provided in this manner. Alternatively or additionally, other possibilities are conceivable.

As a Hct value can now be determined in this manner with a high degree of precision based on the time course of reflectance, correction of the glucose measurement values from the second time interval 164 may be conducted using the known Hct value. As explained above, this correction may be carried out afterward or already included in conversion during the first calculation of the analyte content.

Correction of the glucose concentration taking into account the Hct value and/or another disturbance variable, as stated above, may be carried out using one or more correction functions. For example, a correction function in the form of a correction equation may be used in which the measured glucose concentration is corrected using correction terms dependent on Hct value and/or other disturbance variables. As such, one or more correction factors and/or one or more correction offsets may be used. As explained above, a correction offset that is dependent on Hct value also can be referred to as a disturbance quantity. Specifically, correction of the glucose concentration for the Hct value may be conducted by addition or subtraction of a correction offset, where the correction offset is a function of the Hct value and/or another kind of disturbance variable. It has been found in practice that correction of the glucose concentration for the Hct value may be conducted, for example, according to the following formula:

$$c(Gluc)\text{corr} = c(Gluc) + m * Hct^i + n \quad (2)$$

In this case, c(Gluc)corr is corrected glucose concentration, and c(Gluc) is the measured glucose concentration. The terms m and i are correction terms of the correction function to be experimentally ascertained, and these also may be dependent on the temperature and glucose concentration per se.

It is to be noted that the aforementioned example of a correction of the Hct value and/or another disturbance variable is only to be understood as an illustration. Numerous other possible corrections are also conceivable. Specifically, an example is given above of a two-step method in which the Hct value is first determined according to Formula (1) from the sudden wetting-induced change, and a corrected glucose concentration is then determined according to Formula (2) from the Hct value. Formulas (1) and (2) also can be combined into a one-step method in which a corrected glucose concentration is directly calculated from the sudden wetting-induced change and the glucose concentration.

Many further possibilities are also conceivable. In a further simplification, for example, the Hct dependency of the system could be determined independently from glucose concentration based on the sudden wetting-induced decreases in reflectance.

A technical implementation of the correction may be conducted by a simple method by, for example, using the data processing unit 142. As explained above, the correction may consist of simple addition or subtraction of one or more derivatives determined in experiments per glucose concentration Hct value as a glucose reference measurement. For this purpose, one or more correction terms and/or correction functions may be deposited in the test unit 112 in the data storage unit 144. One or more dependency curves and/or dependency tables describing the correction could be deposited in, for example, the form of polygon courses or hypersurfaces. Using the ascertained Hct values and the known glucose concentration at the end of measurement, this correction amount can be added or subtracted.

Figure 8:
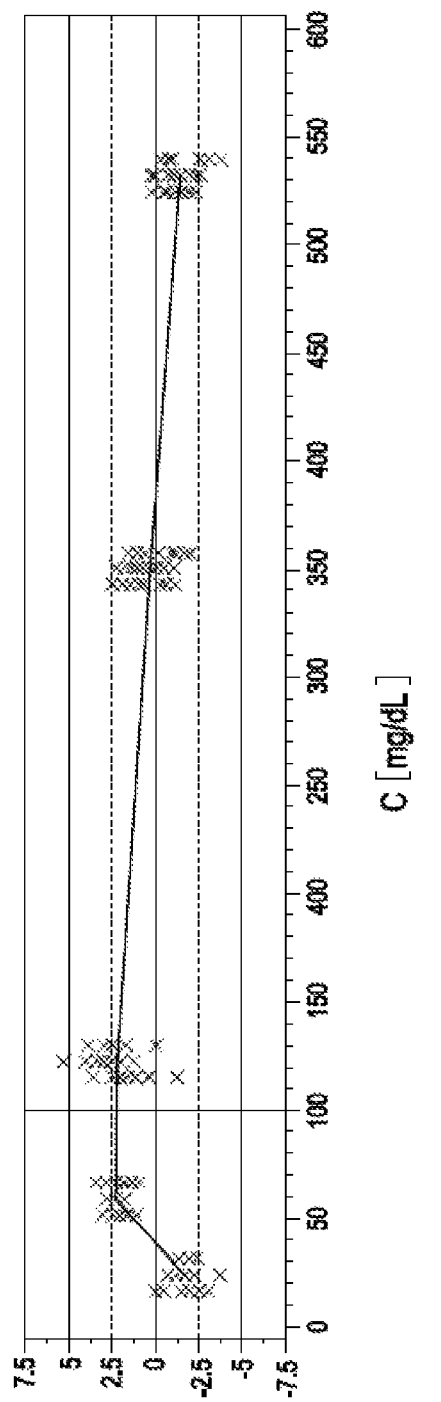
FIG. 8 shows an artificially generated example of dependency of deviation in glucose concentration versus a reference method in dependency of Hct as a disturbance variable.

FIG. 8 shows deposition of corrections for illustrative purposes. An artificially generated example is shown of the dependency of a deviation Δ in the measured uncorrected glucose concentration from an actual glucose concentration determined using a reliable reference method. In this case, blood samples with different Hct values can be produced (i.e., 25, 30, 35, 43, 50, 55, 60 and 65% . . . values should cover the maximum range typically occurring in practice). Such blood samples likewise can be prepared with different glucose concentrations (i.e., 0-20 mg/dL, 50 mg/dL, 100 mg/dL, 300 mg/dL and 450 mg/dL). The actual glucose concentrations are measured for example with a laboratory unit or in another manner, and the deviation Δ from the respective uncorrected glucose concentration ascertained by means of the at least one optical measurement value (for example reflectance) was determined. Specifically, FIG. 8 shows an example using a Hct value of 30%, with the horizontal axis showing the actual glucose concentrations c of the sample in mg/dL ascertained using the reliable reference method. The vertical axis shows the deviations between the uncorrected glucose concentrations determined based on reflectance and the actual glucose concentrations for a number of different experiments respectively. For actual glucose concentrations below 100 mg/dL, the deviations Δ are given as absolute values in mg/dL, and for actual glucose concentrations above 100 mg/dL, they are shown in percent. Such curves or polygon courses, as shown in FIG. 8, may be successively determined for numerous hematocrit values, so that when the curves are placed adjacent to one another, this gives rise to a hypersurface, on which the actual concentration c is shown on a first axis, the Hct value on a second axis, and the deviation Δ on a third axis. Such hypersurfaces may be deposited by means of individual values in table, analytical, or other form in the data storage unit 144, so that for each Hct value and each glucose concentration the relevant Δ can be determined and the Hct correction can be subtracted from or added to the uncorrected measured glucose concentration according to the aforementioned equations (1) and (2) to arrive at a corrected value for glucose concentration. The Hct dependency is over different batches of the reagent element 124 at least largely stable. The ascertained correction values therefore are universally valid for a combination of a test unit 112 and a test element 114 with a specified reagent element 124.

Figure 9:
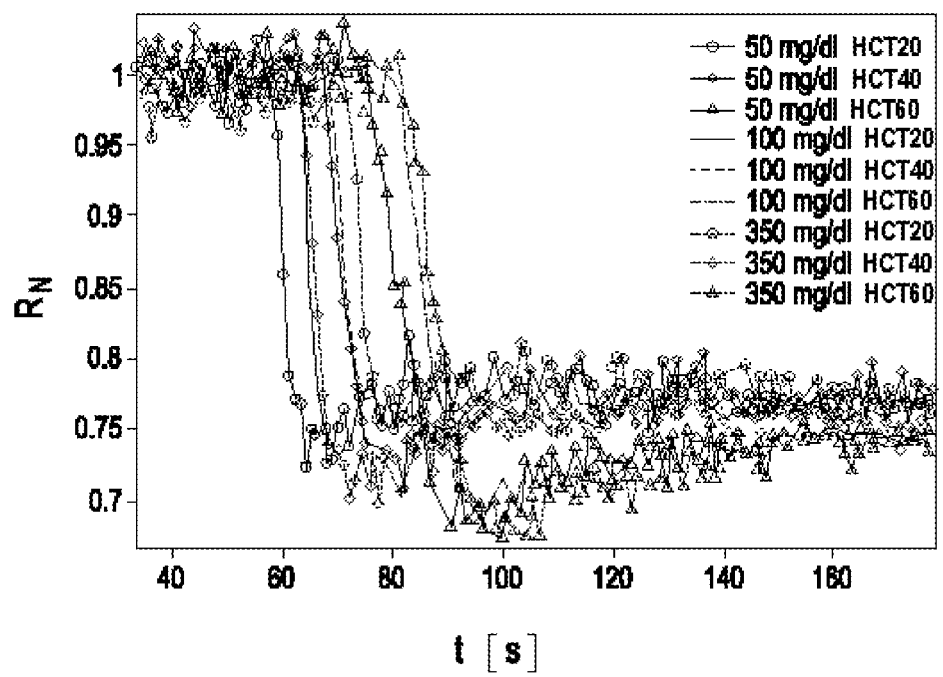
FIG. 9 shows a time course of standardized reflectance values measurement on a cNAD-based reagent element at different blood glucose concentrations and Hct.
Figure 10:
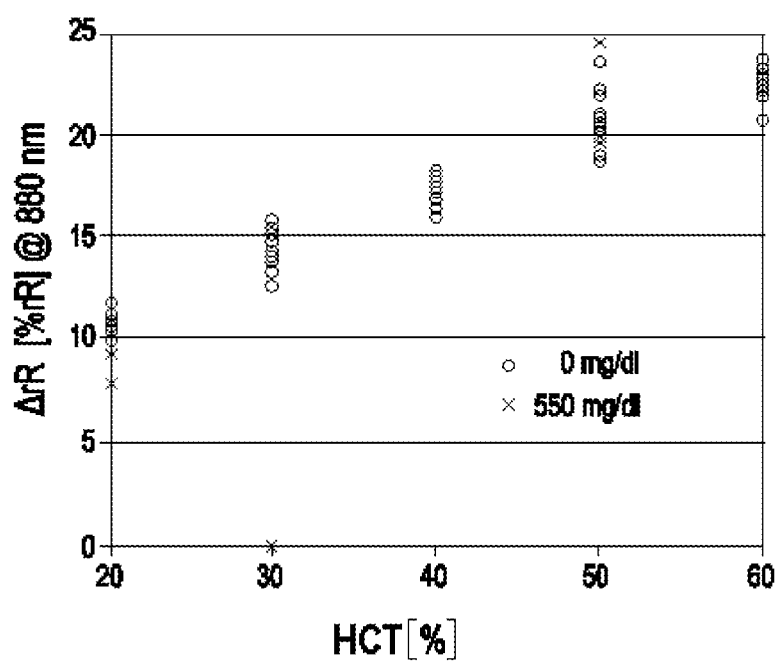
FIG. 10 shows a correlation between sudden wetting-induced change and Hct in measurement of samples with different blood glucose concentrations.

FIGS. 9-10 show further embodiments of measurements that clarify the inventive concept of the present disclosure. In these measurements, as was the case for those shown above, a test element 114 was modified, although this element in the embodiment shown had a reagent element 124 with a cNAD coenzyme, such as that described in von Ketteler et al. (2012), supra.

Analogously to the above-described FGIS. 3 and 6, the time course of a diffuse reflectance curve was again recorded, and sudden wetting-induced changes ΔrR were measured. Here, FIG. 9 shows the time course of standardized reflectance RN (i.e., diffuse reflectance curves), which are initially standardized to the reflectance value 1. The time t in seconds s is plotted on the horizontal axis. The measurements were conducted on the aforementioned cNAD reagent element, for which the time courses and sudden wetting-induced changes were determined at a wavelength of 600 nm. The time courses are shown for various blood glucose concentrations, indicated in the legend, of 50 mg/dL, 100 mg/dL and 350 mg/dL, and samples with respective Hct values (indicated here as HO) of 20%, 40% and 60% were used for each glucose concentration. The blood glucose concentrations were determined with an excitation wavelength of 365 nm.

The measurements in FIG. 9 show that sudden wetting-induced changes vary sharply in height and time point. Specifically, the sudden wetting-induced change occurs for samples with the same blood glucose concentration later at higher Hct values than at lower Hct values. In addition, the sudden wetting-induced change is considerably more pronounced in samples with the same blood glucose concentration at higher Hct values than at lower Hct values.

This correlation is shown in FIG. 10. Again for a cNAD-reagent element, sudden wetting-induced changes ΔrR given in % relative reflectance (rR) are shown on the vertical axis. The horizontal axis shows the relevant Hct values in percent. Measurements of sudden wetting-induced changes were conducted using an infrared LED with an emission wavelength of 880 nm. The measurements were conducted on blood samples with Hct values of 20%, 30%, 40%, 50% and 60%, for respective blood glucose concentrations of 0 mg/dL and 550 mg/dL, as shown in the legend.

The measurements shown in FIG. 10 clarify the finding, already apparent in FIG. 9, that the sudden wetting-induced change, with the exception of unavoidable anomalies in the measurement values, is essentially independent of the blood glucose concentration, even over the entire range relevant in practice up to blood glucose concentrations of 550 mg/dL. However, the sudden wetting-induced change, as shown by the measurements in FIG. 9, is clearly dependent on the respective Hct value. As explained above, it again can be stated, based on detecting sudden wetting-induced changes, that Hct value is not dependent on blood glucose concentration for the cNAD reagent element as well. This finding of non-dependency may then be used to determine a corrected blood glucose concentration c(Gluc)corr by, for example, means of a correction algorithm according to equation (2) above.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

LISTING OF REFERENCE NUMBERS

110 Device for determining a concentration of an analyte in the blood
112 Test unit
114 Test element
116 Test strip
118 Test element holder
120 Blood sample
122 Application site
124 Reagent element
126 Reagent element field
128 Optical detection device
130 Interrogating light source
132 Interrogating light beam
134 Detector
136 Response light beam
138 Evaluation device
140 Data line
142 Data processing device
144 Data storage
146 Operating element
148 Display element
150 First light-emitting diode (LED1)
152 Second light-emitting diode (LED2)
154 First light-emitting diode A (LED1A)
156 First light-emitting diode B (LED1B)
158 First time interval
160 Sudden wetting-induced change
162 Break
164 Second time interval
166 Capillary element
168 Carrier element
170 Spacer
172 Covering film
174 Opening
176 Separating element
178 Separating layer 180 Reflecting surface
182 Hematocrit 25%
184 Hematocrit 55%

The invention claimed is:

1. A method of determining at least one analyte concentration in a body fluid sample, the method comprising the steps of:
providing at least one test element that comprises at least one reagent element configured for at least one optically detectable detection reaction in the presence of the analyte;
applying the body fluid sample to the test element;
detecting a time course of at least one optical measurement variable of the reagent element;
determining at least one disturbance variable value in the body fluid sample from at least one first time interval of the time course of the at least one optical measurement variable; and
determining the at least one analyte concentration from at least one second time interval of the time course of the at least one optical measurement variable,
wherein a time interval is a quantity of measurement time points comprising at least two measurement time points,
wherein during the detecting of the time course of the at least one optical measurement variable in the first time interval and the second time interval, the reagent element is irradiated by at least one interrogating light beam from at least one interrogating light source, and wherein at least one response light beam from the reagent element is detected by at least one detector, and wherein the time course of at least one optical measurement variable in the first time interval includes a sudden wetting-induced change in the optical measurement variable.

2. The method as claimed in claim 1, wherein the first time interval is an initial time interval of the time course, and wherein the second time interval is subsequent to the first time interval.

3. The method of claim 1, wherein the at least one optical measurement variable is determined at at least one first wavelength, and wherein a wetting time point at which the body fluid sample reaches and wets the reagent element is determined from a change in the optical measurement variable after the body fluid sample is applied to the test element.

4. The method of claim 1, wherein at least one correction or compensation is ascertained by means of the disturbance variable value, and wherein a corrected at least one analyte concentration is ascertained from the second time interval taking into account the correction or compensation.

5. The method of claim 1, wherein a change in the at least one optical measurement variable in the second time interval is detected, and wherein the optical measurement variable determined at a time point at which a temporal change in the optical measurement value was below a preset threshold value is used to determine the at least one analyte concentration.

6. The method of claim 1, wherein the body fluid sample is blood and is applied to at least one application site on the test element, wherein the blood or components thereof are transferred from the application site to the reagent element, and wherein the at least one analyte concentration is a glucose concentration.

7. The method of claim 6, wherein the disturbance variable value is a hematocrit value.

8. The method of claim 1, wherein the at least one optical measurement variable is a reflectance value.

9. A method of determining at least one analyte concentration in a body fluid sample, the method comprising the steps of:
providing at least one test element that comprises at least one reagent element configured for at least one optically detectable detection reaction in the presence of the analyte;
applying the body fluid sample to the test element;
detecting a time course of at least one optical measurement variable of the reagent element;
determining at least one disturbance variable value in the body fluid sample from at least one first time interval of the time course of the at least one optical measurement variable; and
determining the at least one analyte concentration from at least one second time interval of the time course of the at least one optical measurement variable,
wherein a time interval is a quantity of measurement time points comprising at least two measurement time points,
wherein during the detecting of the time course of the at least one optical measurement variable in the first time interval and the second time interval, the reagent element is irradiated by at least one interrogating light beam from at least one interrogating light source, and wherein at least one response light beam from the reagent element is detected by at least one detector, wherein the interrogating light beam has a same wavelength and/or a same spectral properties in the first time interval and the second time interval.

10. The method of claim 9, wherein the response light beam has one or both of the same wavelength and the same spectral properties in the first time interval and the second time interval.

11. A device for determining at least one analyte concentration in a body fluid sample, the device comprising:
at least one test element, wherein the test element has at least one reagent element configured for at least one optically detectable detection reaction in the presence of the at least one analyte, and wherein the body fluid sample may be applied to the test element;
at least one interrogating light source for providing at least one interrogating light beam;
at least one optical detection device, wherein the optical detection device is configured for detecting a time course of at least one optical measurement variable of the reagent element;
at least one evaluation device, wherein the evaluation device is configured for determining at least one disturbance variable value in the body fluid sample from at least one first time interval of the time course of the at least one optical measurement variable, and wherein the evaluation device is further configured for determining the at least one analyte concentration from at least one second time interval of the time course, wherein a time interval is a quantity of measurement time points comprising at least two measurement time points,
wherein during the detecting of the at least one optical measurement variable in the first time interval and the second time interval, the reagent element is irradiated by the at least one interrogating light beam from the at least one interrogating light source, and wherein at least one response light beam from the reagent element is detected by at least one optical detection device, and wherein the time course of the optical measurement variable in the first time interval includes a sudden wetting-induced change in the optical measurement variable.

12. The device of claim 11, wherein the test element is a test strip and the device further comprises at least one test strip holder, wherein at least one test strip in the at least one test strip holder can be placed in an application position, wherein in the application position, a user can apply the body fluid sample to at least one application site of the test strip, and wherein the test strip further comprises at least one capillary element for transferring the body fluid sample or components thereof from the at least one application site to the reagent element.

13. The device of claim 12, wherein at least one separating element for separating at least one component from the body fluid sample is configured between the capillary element and the reagent element.

14. The device of claim 11, wherein the body fluid sample is blood, and wherein the at least one analyte concentration is a glucose concentration.

15. The device of claim 14, wherein the disturbance variable value is a hematocrit value.

16. The device of claim 14, wherein the at least one evaluation device is further configured for using the disturbance variable value to correct or compensate the glucose concentration.

17. The device of claim 11, wherein the at least one optical measurement variable is a reflectance value.

18. A device for determining at least one analyte concentration in a body fluid sample, the device comprising:

at least one test element, wherein the test element has at least one reagent element configured for at least one optically detectable detection reaction in the presence of the at least one analyte, and wherein the body fluid sample may be applied to the test element;

at least one interrogating light source for providing at least one interrogating light beam;

at least one optical detection device, wherein the optical detection device is configured for detecting a time course of at least one optical measurement variable of the reagent element;

at least one evaluation device, wherein the evaluation device is configured for determining at least one disturbance variable value in the body fluid sample from at least one first time interval of the time course of the at least one optical measurement variable, and wherein the evaluation device is further configured for determining the at least one analyte concentration from at least one second time interval of the time course, wherein a time interval is a quantity of measurement time points comprising at least two measurement time points, wherein during the detecting of the at least one optical measurement variable in the first time interval and the second time interval, the reagent element is irradiated by the at least one interrogating light beam from the at least one interrogating light source, and wherein at least one response light beam from the reagent element is detected by at least one optical detection device, wherein the at least one optical detection device is configured for detecting the at least one optical measurement variable in the first time interval and the second time interval at the same wavelength.

* * * * *